(12) United States Patent
Rekhi et al.

(10) Patent No.: US 9,452,163 B2
(45) Date of Patent: *Sep. 27, 2016

(54) ABUSE RESISTANT PHARMACEUTICAL COMPOSITIONS

(71) Applicant: Recro Gainesville LLC, Gainesville, GA (US)

(72) Inventors: Gurvinder Singh Rekhi, Suwanee, GA (US); Richard Sidwell, Cumming, GA (US)

(73) Assignee: Recro Gainesville LLC, Gainesville, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/851,019

(22) Filed: Sep. 11, 2015

(65) Prior Publication Data

US 2016/0074385 A1    Mar. 17, 2016

Related U.S. Application Data

(63) Continuation of application No. 14/484,761, filed on Sep. 12, 2014, now Pat. No. 9,132,096.

(51) Int. Cl.
*A61K 31/485* (2006.01)
*A61K 9/16* (2006.01)
(Continued)

(52) U.S. Cl.
CPC .......... *A61K 31/485* (2013.01); *A61K 9/1641* (2013.01); *A61K 9/1676* (2013.01); *A61K 9/5078* (2013.01); *A61K 9/5084* (2013.01); *A61K 47/10* (2013.01)

(58) Field of Classification Search
CPC .. A61K 9/141; A61K 9/1676; A61K 31/485; A61K 47/10; A61K 9/5026
See application file for complete search history.

(56) References Cited

U.S. PATENT DOCUMENTS

| 3,980,766 A | 9/1976 | Shaw et al. |
| 4,070,494 A | 1/1978 | Hoffmeister et al. |

(Continued)

FOREIGN PATENT DOCUMENTS

| WO | 95/20947 A1 | 8/1995 |
| WO | 96/08253 A1 | 3/1996 |

(Continued)

OTHER PUBLICATIONS

Findings of Fact and Conclusions of Law, In re Oxycontin Antitrust Litigation, Purdue Pharma L.P. et al. v. Teva Pharmaceuticals, USA, Inc., 1:11 Civ. 2037 (SDNY), filed Jan. 14, 2014 (115 pages).

(Continued)

*Primary Examiner* — Lakshmi Channavajjala
(74) *Attorney, Agent, or Firm* — Pepper Hamilton LLP

(57) ABSTRACT

The present invention relates to a composition comprising pharmaceutical active ingredients which are susceptible to, or have potential for, abuse. The invention provides an oral pharmaceutical composition comprising a first population of beads and a second population of beads. The first bead population comprises a pharmaceutically active ingredient susceptible to, or having the potential for, abuse. The second bead population comprises a gelling agent and a coating substantially surrounding the gelling agent, but containing no pharmaceutically active ingredient. The first bead population and the second bead population are physically separable, but visually indistinguishable to the naked eye. Upon ingress of water into the second population of beads, the gelling agent is caused to swell forming a viscous mass inhibiting or preventing the extraction of the active ingredient.

6 Claims, 9 Drawing Sheets

(51) Int. Cl.
*A61K 47/10* (2006.01)
*A61K 9/50* (2006.01)

(56) References Cited

U.S. PATENT DOCUMENTS

| | | |
|---|---|---|
| 4,457,933 A | 7/1984 | Gordon et al. |
| 4,684,516 A | 8/1987 | Bhutani |
| 4,839,177 A | 6/1989 | Colombo et al. |
| 5,132,142 A | 7/1992 | Jones et al. |
| 5,149,538 A | 9/1992 | Granger et al. |
| 5,236,714 A | 8/1993 | Lee et al. |
| 5,411,745 A | 5/1995 | Oshlack et al. |
| 5,422,123 A | 6/1995 | Conte et al. |
| 5,478,577 A | 12/1995 | Sackler et al. |
| 5,639,476 A | 6/1997 | Oshlack et al. |
| 5,654,009 A | 8/1997 | Hata et al. |
| 5,773,031 A | 6/1998 | Shah et al. |
| 5,866,164 A | 2/1999 | Kuczynski et al. |
| 5,958,459 A | 9/1999 | Chasin et al. |
| 6,066,339 A | 5/2000 | Stark et al. |
| 6,077,533 A | 6/2000 | Oshlack et al. |
| 6,103,261 A | 8/2000 | Chasin et al. |
| 6,143,322 A | 11/2000 | Sackler et al. |
| 6,228,398 B1 | 5/2001 | Devane et al. |
| 6,228,863 B1 | 5/2001 | Palermo et al. |
| 6,245,357 B1 | 6/2001 | Edgren et al. |
| 6,277,384 B1 | 8/2001 | Kaiko et al. |
| 6,309,668 B1 | 10/2001 | Bastin et al. |
| 6,316,031 B1 | 11/2001 | Oshlack et al. |
| 6,372,255 B1 | 4/2002 | Saslawski et al. |
| 6,419,959 B1 | 7/2002 | Walter et al. |
| 6,475,494 B2 | 11/2002 | Kaiko et al. |
| 6,488,963 B1 | 12/2002 | McGinity et al. |
| 6,491,945 B1 | 12/2002 | Childers et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,709,678 B2 | 3/2004 | Gruber |
| 6,733,783 B2 | 5/2004 | Oshlack et al. |
| 6,905,709 B2 | 6/2005 | Oshlack et al. |
| 7,060,293 B1 | 6/2006 | Oshlack et al. |
| 7,125,561 B2 | 10/2006 | Sackler |
| 7,141,250 B2 | 11/2006 | Oshlack et al. |
| 7,144,587 B2 | 12/2006 | Oshlack et al. |
| 7,157,103 B2 | 1/2007 | Sackler |
| 7,172,767 B2 | 2/2007 | Kaiko et al. |
| 7,201,920 B2 | 4/2007 | Kumar et al. |
| 7,316,821 B2 | 1/2008 | Oshlack et al. |
| 7,332,182 B2 | 2/2008 | Sackler |
| 7,399,488 B2 | 7/2008 | Hirsh et al. |
| 7,419,686 B2 | 9/2008 | Kaiko et al. |
| 7,510,726 B2 | 3/2009 | Kumar et al. |
| 7,514,100 B2 | 4/2009 | Oshlack et al. |
| 7,658,939 B2 | 2/2010 | Oshlack et al. |
| 7,682,632 B2 | 3/2010 | Oshlack et al. |
| 7,718,192 B2 | 5/2010 | Oshlack et al. |
| 7,727,557 B2 | 6/2010 | Sackler |
| 7,749,542 B2 | 7/2010 | Kaiko et al. |
| 7,771,707 B2 | 8/2010 | Hirsh et al. |
| 7,776,314 B2 | 8/2010 | Bartholomaus et al. |
| 7,790,215 B2 | 9/2010 | Sackler et al. |
| 7,842,307 B2 | 11/2010 | Oshlack et al. |
| 7,842,309 B2 | 11/2010 | Oshlack et al. |
| 7,842,311 B2 | 11/2010 | Oshlack et al. |
| 7,879,362 B2 | 2/2011 | Castan et al. |
| 7,914,818 B2 | 3/2011 | Breder et al. |
| 7,943,174 B2 | 5/2011 | Oshlack et al. |
| 7,968,119 B2 | 6/2011 | Farrell |
| 7,981,439 B2 | 7/2011 | Kumar et al. |
| 8,017,148 B2 | 9/2011 | Sackler |
| 8,097,278 B2 | 1/2012 | Sackler |
| 8,101,630 B2 | 1/2012 | Kumar et al. |
| 8,105,631 B2 | 1/2012 | Kaiko et al. |
| 8,114,383 B2 | 2/2012 | Bartholomaus et al. |
| 8,187,636 B2 | 5/2012 | Soscia et al. |
| 8,231,898 B2 | 7/2012 | Oshlack et al. |
| 8,309,060 B2 | 11/2012 | Bartholomaus et al. |
| 8,337,888 B2 | 12/2012 | Wright et al. |
| 8,361,499 B2 | 1/2013 | Oshlack et al. |
| 8,389,007 B2 | 3/2013 | Wright et al. |
| 8,409,616 B2 | 4/2013 | Kumar et al. |
| 8,414,919 B2 | 4/2013 | Gervais et al. |
| 8,445,018 B2 | 5/2013 | Habib et al. |
| 8,445,023 B2 | 5/2013 | Guimberteau et al. |
| 8,486,448 B2 | 7/2013 | Rahmouni et al. |
| 8,486,449 B2 | 7/2013 | Rahmouni et al. |
| 8,524,275 B2 | 9/2013 | Oshlack et al. |
| 8,529,948 B1 | 9/2013 | Wright et al. |
| 8,609,683 B2 | 12/2013 | Wright et al. |
| 8,652,497 B2 | 2/2014 | Sackler |
| 8,652,515 B2 | 2/2014 | Sackler |
| 8,652,529 B2 | 2/2014 | Guimberteau et al. |
| 8,685,447 B2 | 4/2014 | Rahmouni et al. |
| 8,691,270 B2 | 4/2014 | Rahmouni et al. |
| 2003/0004177 A1 | 1/2003 | Kao et al. |
| 2003/0064122 A1 | 4/2003 | Goldberg et al. |
| 2003/0068375 A1 | 4/2003 | Wright et al. |
| 2003/0077320 A1 | 4/2003 | Childers et al. |
| 2004/0091528 A1 | 5/2004 | Rogers et al. |
| 2005/0186147 A1 | 8/2005 | Tamarkin et al. |
| 2005/0214223 A1 | 9/2005 | Bartholomaeus et al. |
| 2006/0039864 A1 | 2/2006 | Bartholomaus et al. |
| 2006/0099256 A1 | 5/2006 | Price et al. |
| 2006/0110327 A1 | 5/2006 | Emigh et al. |
| 2006/0177380 A1 | 8/2006 | Emigh et al. |
| 2006/0240105 A1 | 10/2006 | Devane et al. |
| 2007/0003617 A1 | 1/2007 | Fischer et al. |
| 2007/0184115 A1 | 8/2007 | Mamajiwalla et al. |
| 2007/0202049 A1 | 8/2007 | Guimberteau et al. |
| 2007/0224129 A1 | 9/2007 | Guimberteau et al. |
| 2007/0231268 A1 | 10/2007 | Emigh et al. |
| 2007/0264346 A1 | 11/2007 | Guimberteau et al. |
| 2008/0008659 A1 | 1/2008 | Guimberteau et al. |
| 2008/0026070 A1 | 1/2008 | Bonnet-Gonnet |
| 2008/0063725 A1 | 3/2008 | Guimberteau et al. |
| 2008/0152595 A1 | 6/2008 | Emigh et al. |
| 2008/0193540 A1 | 8/2008 | Soula et al. |
| 2008/0248113 A1 | 10/2008 | Bartholomaus et al. |
| 2008/0317847 A1 | 12/2008 | Macgregor |
| 2009/0004281 A1 | 1/2009 | Nghiem et al. |
| 2009/0081287 A1 | 3/2009 | Wright et al. |
| 2009/0175937 A1 | 7/2009 | Rahmouni et al. |
| 2009/0220613 A1 | 9/2009 | Odidi et al. |
| 2009/0221621 A1 | 9/2009 | Sathyan et al. |
| 2009/0258066 A1 | 10/2009 | Venkatesh et al. |
| 2009/0304787 A1 | 12/2009 | Odidi et al. |
| 2009/0304793 A1 | 12/2009 | Boehm |
| 2010/0092553 A1 | 4/2010 | Guimberteau et al. |
| 2010/0111879 A1 | 5/2010 | Tamarkin et al. |
| 2010/0143481 A1 | 6/2010 | Shenoy et al. |
| 2010/0203130 A1 | 8/2010 | Tygesen et al. |
| 2010/0239667 A1 | 9/2010 | Hemmingsen et al. |
| 2010/0266701 A1 | 10/2010 | Guimberteau et al. |
| 2011/0077238 A1 | 3/2011 | Leech et al. |
| 2011/0200681 A1 | 8/2011 | Habib et al. |
| 2012/0065221 A1 | 3/2012 | Babul |
| 2012/0108622 A1 | 5/2012 | Wright et al. |
| 2012/0131463 A1 | 5/2012 | Lefler |
| 2012/0141583 A1 | 6/2012 | Mannion et al. |
| 2012/0178771 A1 | 7/2012 | Babul et al. |
| 2012/0202839 A1 | 8/2012 | Emigh et al. |
| 2012/0207825 A1 | 8/2012 | Roy et al. |
| 2012/0208773 A1 | 8/2012 | Duffield et al. |
| 2012/0225122 A1 | 9/2012 | Hamed et al. |
| 2012/0321674 A1 | 12/2012 | Vachon et al. |
| 2012/0321716 A1 | 12/2012 | Vachon et al. |
| 2013/0005823 A1 | 1/2013 | Emigh et al. |
| 2013/0022646 A1 | 1/2013 | Rudnic et al. |
| 2013/0028970 A1 | 1/2013 | Schwier et al. |
| 2013/0038267 A1 | 2/2013 | Jiang et al. |
| 2013/0072514 A1 | 3/2013 | Boehm et al. |
| 2013/0129825 A1 | 5/2013 | Billoet |
| 2013/0171257 A1 | 7/2013 | Kumar et al. |
| 2013/0195935 A1 | 8/2013 | Bartholomaus et al. |

(56) References Cited

U.S. PATENT DOCUMENTS

| | | |
|---|---|---|
| 2013/0209560 A1 | 8/2013 | Hamed et al. |
| 2013/0217716 A1 | 8/2013 | Wright et al. |
| 2013/0245055 A1 | 9/2013 | Wright et al. |
| 2013/0261143 A1 | 10/2013 | Wright et al. |
| 2013/0261144 A1 | 10/2013 | Wright et al. |
| 2013/0303494 A1 | 11/2013 | Wright et al. |
| 2013/0317051 A1 | 11/2013 | Oshlack et al. |
| 2014/0008831 A1 | 1/2014 | Yang et al. |
| 2014/0030249 A1 | 1/2014 | Duffield et al. |
| 2014/0037728 A1 | 2/2014 | Tengler et al. |
| 2014/0155425 A1 | 6/2014 | Sackler |
| 2014/0155426 A1 | 6/2014 | Sackler |
| 2014/0213606 A1 | 7/2014 | Wright et al. |

FOREIGN PATENT DOCUMENTS

| | | |
|---|---|---|
| WO | 98/010762 A2 | 3/1998 |
| WO | 99/018967 A1 | 4/1999 |
| WO | 0025752 A1 | 5/2000 |
| WO | 01/49276 A2 | 7/2001 |
| WO | 03/013479 | 2/2003 |
| WO | 03/082243 A1 | 10/2003 |
| WO | 2005/000310 A1 | 1/2005 |
| WO | 2007/096906 A2 | 8/2007 |
| WO | 2007/106550 A2 | 9/2007 |
| WO | 2007/107787 A2 | 9/2007 |
| WO | 2007/150074 A2 | 12/2007 |
| WO | 2007/150075 A2 | 12/2007 |
| WO | 2008/001341 A1 | 1/2008 |
| WO | 2008/021394 A2 | 2/2008 |
| WO | 2008/023261 A1 | 2/2008 |
| WO | 2008/024490 A2 | 2/2008 |
| WO | 2008/033523 | 3/2008 |
| WO | 2008/122993 A1 | 10/2008 |
| WO | 2009/014533 A1 | 1/2009 |
| WO | 2011/132167 A1 | 10/2011 |
| WO | 2012/112952 A1 | 8/2012 |
| WO | 2012/131463 A2 | 10/2012 |
| WO | 2013/038267 A1 | 3/2013 |
| WO | 2013/038268 A1 | 3/2013 |
| WO | 2013/128276 A2 | 9/2013 |
| WO | 2014/059512 A1 | 4/2014 |

OTHER PUBLICATIONS

International Search Report dated Nov. 23, 2015 issued for International Application No. PCt/IB2015/056993 (10 pages).

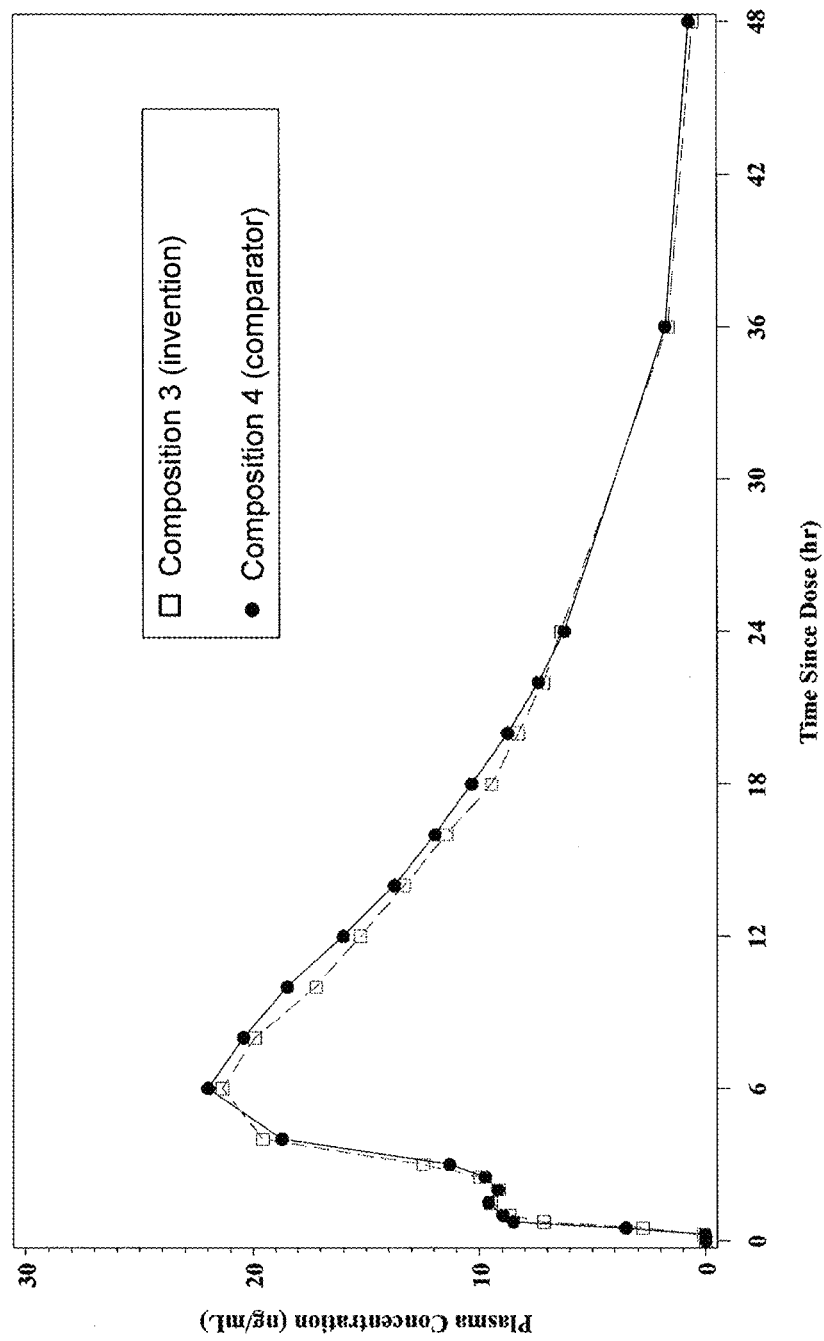

ABUSE RESISTANT PHARMACEUTICAL COMPOSITIONS

CROSS-REFERENCE TO RELATED APPLICATION

This application is a continuation application of and claims priority to pending non-provisional U.S. patent application Ser. No. 14/484,761 filed on Sep. 12, 2014, which is hereby incorporated by reference in its entirety.

FIELD OF THE INVENTION

The present invention relates to a composition comprising pharmaceutical active ingredients which are susceptible to, or have potential for, abuse. The composition of the invention is adapted to be abuse resistant so as to reduce or eliminate such abuse.

BACKGROUND OF THE INVENTION

It is widely known that certain categories of drugs such as analgesics (e.g. opioids), sedatives (e.g. benzodiazepines) and stimulants (e.g. amphetamines) have potential to be misused or abused if they are not used as intended or as prescribed.

In the case of intentional misuse or abuse a person may attempt to extract the active ingredient from the commercial dosage form in order to concentrate it and take a larger amount than prescribed or to take the drug in a different manner to that prescribed, the object being to produce a euphoric "high" or some other pharmacological effect other than that produced when the product is used as intended.

One mode of abuse involves crushing a dosage form and inhaling or snorting the resultant powder. Another mode of abuse involves extracting the active ingredient with water, alcohol or some other solvent to produce a liquid form for injection.

As part of a wider effort to address the issue of deliberate misuse or abuse of prescription drugs the US Food and Drug Administration has issued a draft guidance for industry on abuse-deterrent opioids (see "Guidance for Industry, Abuse-Deterrent Opioids—Evaluation and Labeling, Draft Guidance" US Dept. of Health and Human Services, Food and Drug Administration, Center for Drug Evaluation and Research, January, 2013). The draft guidance provides some background to the problem of opioid abuse and discusses various formulation approaches that may be used in attempts to reduce or mitigate abuse potential. Furthermore, it details the studies, and other requirements, necessary to support labelling which contains abuse deterrent or reduction claims.

Various abuse deterrent or abuse reducing approaches are known in the prior art.

U.S. Pat. No. 7,201,920 (Acura Pharmaceuticals, Inc) discloses an abuse deterrent dosage form wherein an active ingredient is combined with a polymer (gel forming agent) to form a matrix. Nasal irritants and/or emetics are also incorporated into the dosage form.

U.S. Pat. No. 7,776,314 (Grunenthal GmbH) discloses a solid administration form, protected from parenteral abuse and containing at least one viscosity-increasing agent in addition to one or more active substances that have parenteral abuse potential. According to claim 1, the viscosity-increasing agent is present in a quantity equal to or greater than 5 mg per dosage form and such that an aqueous extract obtained from the dosage form with 10 mL of water at 25° C., forms a gel which can still pass through a needle having a diameter of 0.9 mm and remains visually distinguishable when introduced by a needle into a further quantity of an aqueous liquid.

U.S. Pat. No. 8,529,948 (Purdue Pharma LP) discloses a controlled release dosage form comprising a gelling agent in an effective amount to impart a viscosity unsuitable for parenteral or nasal administration to a solubilized mixture formed when the dosage form is crushed and mixed with from about 0.5 to about 10 mL of aqueous liquid. The dosage form may comprise a range of aversive agents (selected from a bittering agent, an irritant, a gelling agent or a combination thereof) to discourage an abuser from tampering with the dosage form.

U.S. Pat. No. 8,652,529 (Flamel Technologies) discloses solid microparticulate oral pharmaceutical forms having a coating layer which assures modified release of the active principle and simultaneously imparts crushing resistance to the coated particles so as to avoid misuse.

It is an object of the present invention to provide an oral pharmaceutical composition which is adapted to reduce or mitigate potential abuse by making it more difficult for the pharmaceutical active ingredient to be extracted and used or administered in a manner other than that originally intended.

It is another object of the invention to provide a pharmaceutical composition which is adapted to reduce or mitigate potential abuse whilst at the same time not compromising the pharmacokinetic characteristics of the composition.

It is a further object of the invention to provide an abuse resistant pharmaceutical composition which goes at least some way to addressing the drawbacks of the prior art.

BRIEF DESCRIPTION OF THE INVENTION

Accordingly, the present invention provides an oral pharmaceutical composition comprising a first population of beads and a second population of beads; said first bead population comprising a pharmaceutically active ingredient susceptible to, or having the potential for, abuse; and said second bead population containing no pharmaceutically active ingredient comprising a gelling agent and a permeable or semi-permeable coating.

The composition is adapted to ensure that the gelling agent contained in the second bead population, upon contact with water or some other liquid, forms a uniform, viscous mass. This may be achieved by means of a permeable or semi-permeable coating which restricts, but does not completely prevent, the ingress of water into the gelling agent-containing beads. The coating may be pH independent or pH dependent. Preferably the coating is a pH independent, semi-permeable coating.

Preferably said first bead population and said second bead population are physically separable, but visually indistinguishable to the naked eye.

Whilst the different populations of beads are physically separable, they should be indistinguishable in order to thwart attempts to isolate the drug containing beads. To that end the beads of the first and second bead populations should be visually indistinguishable to the naked eye in terms of their size, shape and colour etc. Furthermore, the different beads preferably have similar densities.

As set out in greater detail below, when the gelling agent present in the second population of beads is exposed to, or comes in contact with, a liquid such as water, an aqueous material or the like, it is caused to swell. The composition of the invention is designed such that the swelling of the gelling agent does not result in the formation of large semi-solid lumps which may get lodged in the gastrointestinal tract, thus restricting or prevent passage of the dosage form and the active ingredient contained therein. Rather the composition of the invention is adapted to ensure that swelling of the gelling agent gives rise to a more dispersed, relatively uniform, but viscous mass. As described in greater details below, this has the effect of isolating or sequestering the other constituents of the composition, thus reducing or preventing extraction of the active ingredient.

The composition of the present invention has a number of advantages. Firstly, the coating of the gelling agent-containing second bead population provides a physically robust abuse deterrent component which may be readily processed into a final dosage form i.e. mixing and blending of the different populations of beads—an important consideration from a manufacturing perspective. Second, when the composition of the invention is taken as intended—i.e. without manipulation of or tampering with the composition as prepared—the presence of the second bead population has minimal or substantially no effect on the delivery of the pharmaceutically active ingredient. In other words pharmacokinetic characteristics of the composition of the invention are substantially the same as those of a similar composition in which the second bead population is not present—i.e. compositions with and without the second bead population should be bioequivalent. Third, the coating on the gelling agent-containing second bead population is adapted to make it more difficult to extract the active ingredient using either small or large volumes of a solvent, such as water.

Because the second bead population embodying the abuse deterrent mechanism is physically distinct from the active ingredient containing beads, and because there is no interaction between the gelling agent and the active ingredient-containing beads until the composition is administered, or an attempt is made to tamper with the composition, the present invention lends itself to the incorporation of essentially any pharmaceutically active ingredient which may benefit from an abuse deterrent or tamper mitigating presentation.

The pharmaceutically active ingredient may be selected from the group consisting of: alfentanil, allylprodine, alphaprodine, amphetamines (e.g., amphetamine, lisdexamphetamine, methamphetamine, methylenedioxymethamphetamine, dextroamphetamine or methylamphetamine), ephedrine, anileridine, benzodiazepines (e.g., bretazenil, clonazepam, cloxazolam, clorazepate, diazepam, fludiazepam, flutoprazepam, lorazepam, midazolam, nimetazepam, nitrazepam, phenazepam, temazepam or clobazam), benzylmorphine, bezitramide, buprenorphine, butorphanol, carfentanil, clonitazene, codeine, desomorphine, dextromoramide, dezocine, diacetylmorphine, diampromide, diamorphone, dihydrocodeine, dihydromorphine, dimenoxadol, dimepheptanol, dimethylthiambutene, diphenoxylate, dioxaphetyl butyrate, diprenorphine, dipipanone, eptazocine, ethoheptazine, ethylmethylthiambutene, ethylmorphine, etonitazene, etorphine, dihydroetorphine, fentanyl, hydrocodone, hydromorphone, β-hydroxy-3-methylfentanyl, hydroxypethidine, isomethadone, ketobemidone, levo-α-acetylmethadol, levorphanol, levophenacylmorphan, lofentanil, meperidine, meptazinol, metazocine, methadone, methylphenidate, metopon, morphine, myrophine, nalmefene, narceine, nicomorphine, norlevorphanol, normethadone, nalorphine, nalbuphene, normorphine, norpipanone, o-methylnaltrexone, opium, oxycodone, oxymorphone, papaveretum, pentazocine, pethidine, phenadoxone, phenomorphan, phenazocine, phenoperidine, piminodine, piritramide, propheptazine, propranolol, promedol, properidine, propoxyphene, remifentanil, sufentanil, tilidine, and tramadol, or pharmaceutically acceptable salts, solvates, ester prodrugs, carboxamide prodrugs, derivatives or active metabolites of any of the foregoing or a mixture thereof.

In one embodiment, the pharmaceutically active ingredient comprises an opioid. When the active ingredient is an opioid it is preferably selected from the group consisting of: buprenorphine, butorphanol, codeine, etorphine, fentanyl, hydrocodone, hydromorphone, morphine, oxycodone, or oxymorphone or a pharmaceutically acceptable salt, ester prodrug, carboxamide prodrug, derivative or active metabolite thereof, or a mixture of the foregoing.

In a further embodiment, the pharmaceutically active ingredient is a μ-opioid agonist or a pharmaceutically acceptable salt, prodrug (especially an ester prodrug or carboxamide prodrug), derivative or active metabolite thereof. In another embodiment, the pharmaceutically active ingredient is a full μ-opioid agonist or a pharmaceutically acceptable salt, prodrug (especially an ester prodrug or carboxamide prodrug), derivative or active metabolite thereof. In another embodiment, the pharmaceutically active ingredient is a partial μ-opioid agonist or a pharmaceutically acceptable salt, prodrug (especially an ester prodrug or carboxamide prodrug), derivative or active metabolite thereof. In another embodiment, the full μ-opioid agonist is a morphinan derivative. In another embodiment, the partial μ-opioid agonist is a morphinan derivative. In another embodiment, the full μ-opioid agonist is a benzomorphan derivative. In another embodiment, the partial μ-opioid agonist is a benzomorphan derivative.

In another embodiment, the pharmaceutically active ingredient is hydrocodone or a pharmaceutically acceptable salt thereof. In another embodiment, the pharmaceutically active ingredient is 17-(cyclobutylmethyl)-4,14-dihydroxy-6-oxo-morphinan-3-carboxamide or a pharmaceutically acceptable salt thereof. In another embodiment, the pharmaceutically active ingredient is (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide or a pharmaceutically acceptable salt thereof.

Gelling agents suitable for use in the present invention include gel forming polymeric materials which swell upon contact with or absorption of a solvent, such as water, alcohol or some aqueous liquid, thus forming a viscous mass. The increase in viscosity in the vicinity of or around the first (drug-containing) bead population makes it difficult, if not impossible, to separate the active ingredient-containing beads or to extract the drug substance from said beads.

Gelling agents suitable for use in the composition of the present invention include hydrophilic cellulosic polymers, polyethylene oxide (PEO) of various molecular weights (for example having an average molecular weight of from about 2,500,000 to about 7,500,000 Daltons), carbomers (polymers of acrylic acid cross-linked with polyalkenyl ethers of sugars or polyalcohols) of various grades and the like. Preferably the gelling agent comprises a polymer selected from the group consisting of hydroxypropyl cellulose, methylcellulose, hydroxypropylmethyl cellulose, polyethylene oxide, sodium carboxymethyl cellulose, sodium alginate and carrageenan. The gelling agent may alternatively or additionally comprise a gum. Suitable gums include for example xanthan gum, guar gum, locust bean gum, gellan gum and glucomannan. The gelling agent may suitably be present in any amount that causes the composition to gel upon exposure to water. The amount of gelling agent present should be such that it does not cause handling problems, such as clogging of coating, encapsulation or tableting equipment. Where the composition is presented in a capsule the gelling agent may be present in amount of at least about 15% (w/w)

of the combined dry weight of active ingredient(s) and excipients present (in other words 15% (w/w) of the overall dry weight of composition), or at least 30 mg per capsule.

The gelling agent-containing beads may further comprise a binder, such as hydroxypropyl cellulose, hydroxymethylpropyl cellulose, poly vinylpyrrolidone or the like.

The coating applied to the gelling agent serves a number of functions. First, it provides a physical barrier essentially separating or sequestering the gelling agent from the other components of the composition, namely the drug-containing first bead population. Secondly, and most important in the context of the abuse deterrent object of the invention, it serves to control (i.e. delay or otherwise limit) the ingress of water into the second bead population, thus restraining the gelling action of the gelling agent.

The coating applied to the gelling agent beads is a coating that is permeable or semi-permeable to water. The coating may be pH dependent or pH independent. Alternatively the coating may comprise a mixture of pH dependent and pH independent materials. Preferably the coating is a pH independent, semi-permeable coating.

Suitable coating materials include cellulosic polymers, such as cellulose acetates, cellulose alkanylates and cellulose acrylates; polyamides; polyurethanes; sulfonated polystyrenes; ammonio methacrylate copolymers such as poly (ethyl acrylate-co-methyl methacrylate-co-trimethylammonioethyl methacrylate chloride) 1:2:0.1 (for example those sold under the trade name Eurdgit® RS (Evonik Industries AG); and methacrylic acid copolymers such as poly(methacrylic acid-co-ethyl acrylate) 1:1 (those sold under the trade name (Eudragit® L (Evonik Industries AG)). Preferably the coating comprises an ammonio methacrylate copolymer or a methacrylic acid copolymer or a mixture thereof. The coating may further comprise plasticizers, pore forming agents, anti-adherents or other excipients that enhance the functioning or application of the coating.

The level of coating applied to the beads can be characterised in terms of weight gain (i.e. the gain in weight of the beads following application of the coating) or in terms of coating thickness. The coating may suitably be present in an amount of about 5% to about 50% polymer weight gain (i.e. polymer weight added expressed as a percent of the weight of uncoated beads; excluding weight of any excipients added with the polymer). When the coating comprises an ammonio methacrylate copolymer or a methacrylic acid copolymer the coating is preferably applied to a polymer weight gain of from about 7.5% to about 25%. Preferably the coating will have a thickness from about 1 to about 100 μm (microns). When the coating comprises an ammonio methacrylate copolymer or a methacrylic acid copolymer the coating is preferably applied to a thickness of about 10 to about 50 μm.

In one preferred embodiment the pharmaceutically active ingredient is hydrocodone, or a pharmaceutically acceptable salt thereof, the gelling agent is polyethylene oxide and the coating applied to the gelling agent-containing beads comprises an ammonio methacrylate copolymer, a methacrylic acid copolymer or a mixture of an ammonio methacrylate copolymer and a methacrylic acid copolymer.

An oral pharmaceutical composition may comprise a first population of beads and a second population of beads; said first bead population comprising a pharmaceutically active ingredient selected from the group consisting of hydrocodone and pharmaceutically acceptable salts thereof; and said second bead population, comprising polyethylene oxide and a semi-permeable coating selected from the group consisting of an ammonio methacrylate copolymer, a methacrylic acid copolymer and mixtures thereof, wherein said second bead population is substantially free of any pharmaceutically active ingredient. Preferably the polyethylene oxide is present in particulate form. The composition second bead population may further comprise povidone.

In one preferred embodiment, an oral pharmaceutical composition may comprise a population of immediate release hydrocodone bitartrate beads, a population of controlled release hydrocodone bitartrate beads and a population of gelling agent-containing beads; said gelling agent-containing beads comprising polyethylene oxide (preferably applied in powder or particulate form), povidone and a semi-permeable coating selected from the group consisting of an ammonio methacrylate compolymer, a methacrylic acid copolymer and mixtures thereof. Preferably the povidone is present in particulate form. Preferably the immediate release beads contain from 1 to 75% w/w of the total amount of hydrocodone bitartrate in the composition with the controlled release beads containing from 25 to 99% w/w of the total amount of hydrocodone bitartrate in the composition.

Also provided is a pharmaceutical dosage form comprising a composition of the invention as described above. The composition may suitably be filled into capsules to produce a finished dosage form. Capsules may be soft or hard capsules of any size or shape. Suitable capsules include for example spherical or elliptical soft elastic capsules; starch, cellulose or gelatin hard capsules (such as Coni-Snap® (Capugsel Belgium NV)) and the like. Appropriate capsules sizes may be selected based on the number and size of the beads to be incorporated into the dosage form, and include capsule sizes 000, 00EL, 0EL, 0, 1, 2, 3, 4, and 5. Alternatively, the composition of the invention may be compressed into tablet form, filled directly into a sachet or presented in some other dosage form suitable for oral administration. Preferably a unit dosage form according to the invention comprises at least about 20 mg of gelling agent per unit (i.e. per capsule or per tablet) and more preferably at least about 30 mg of gelling agent per unit An oral capsule dosage form may contain a composition made up of hydrocodone bitartrate beads and gelling agent-containing beads; said gelling agent-containing beads consisting essentially of sugar spheres, polyethylene oxide, povidone and a semi-permeable coating comprising a polymer selected from the group consisting of an ammonio methacrylate copolymer, a methacrylic acid copolymer and a combination thereof. The gelling agent-containing beads may consist essentially of

| | |
|---|---|
| (i) sugar spheres | 25.0-35.0% w/w |
| (ii) polyethylene oxide | 40.0-50.0% w/w |
| (iii) povidone | 2.5-7.5% w/w |
| (iv) ammonio methacrylate copolymer | 5.0-20.0% w/w |
| (v) silicon dioxide | 1.0-7.5% w/w |
| (vi) talc | 1.0-7.5% w/w. |

In one exemplary dosage form the hydrocodone bitartrate beads consist of hydrocodone bitartrate immediate release beads and hydrocodone bitartrate controlled release beads filled into a capsule with gelling agent containing-beads. The overall composition may consist essentially of

| | |
|---|---|
| (i) hydrocodone bitartrate | 5.0-50.0 mg/capsule |
| (ii) sugar spheres | 65.0-250.0 mg/capsule |
| (iii) hypromellose | 2.0-15.0 mg/capsule |
| (iv) ammonio methacrylate copolymer | 7.5-40.0 mg/capsule |

| | |
|---|---|
| (v) silicon dioxide | 2.5-25.0 mg/capsule |
| (vi) talc | 1.0-7.5 mg/capsule |
| (vii) polyethylene oxide | 30.0-100.0 mg/capsule |
| (vii) povidone | 2.5-12.5 mg/capsule | and wherein 20% of the hydrocodone bitartrate are present in the immediate release beads and 80% of the hydrocodone bitartrate are present in the controlled release beads.

Also provided are methods of treating a subject with a pharmaceutically active ingredient susceptible to, or having the potential for, abuse, comprising the step of administering to a subject in need thereof a pharmaceutically effective amount of a composition or a unit dosage form of the invention as described above. Where the pharmaceutically active ingredient present in the composition is an analgesic the invention provides methods of treating, preventing, reducing or otherwise managing pain, said method comprising administering to a subject in need thereof an analgesically effective amount of a composition or unit dosage form as described above. Preferably said analgesically effective amount is from 5 to 250 mg per unit dosage form.

The invention also provides a process for the manufacture of abuse deterrent beads comprising the steps of applying gelling agent particles and a binder solution, if present, to a substrate to form uncoated gelling agent-containing beads, and coating said gelling agent-containing beads with a water permeable or semi-permeable coating. Preferably the gelling agent particles comprise polyethylene oxide powder and a binder solution of polyvinyl pyrrolidone dissolved in an isopropyl alcohol/water mixture comprising from 10 to 30% w/w water. Preferably the PEO powder and the binder solution are simultaneously applied to the substrate to form the uncoated gelling agent beads.

Abuse deterrent beads prepared according to the foregoing process may be filled into capsules with active ingredient-containing beads or compressed into tablets to form an abuse resistant dosage form.

In a further aspect the invention provides a gelling agent composition suitable for imparting abuse resistant character to a composition comprising a pharmaceutically active ingredient which is susceptible to, or has potential for, abuse, said gelling agent composition comprising a plurality of beads comprising a gelling agent coated with a permeable or semi-permeable coating. Suitable gelling agent compositions are described in detail below. The gelling agent may be polyethylene oxide, preferably applied to a substrate in particulate form along with a binder.

DESCRIPTION OF THE DRAWINGS

FIG. 4 depicts is a graph illustrating the in vivo release of drug (mean plasma concentrations) from another composition of the invention compared to that of a comparator composition which does not contain a gelling agent component.

DETAILED DESCRIPTION OF THE INVENTION

Figure 1:
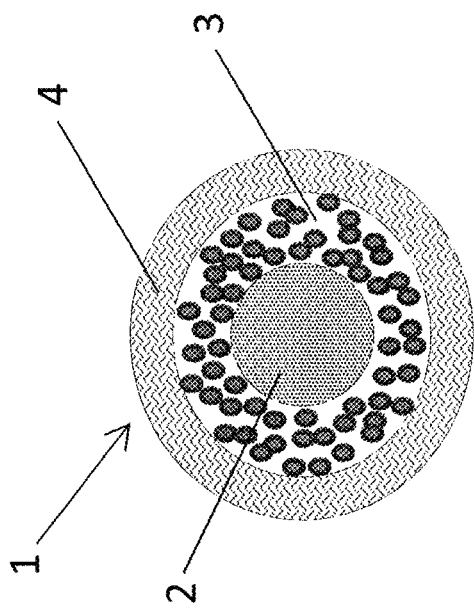
FIG. 1 is a schematic representation of a gelling agent-containing, abuse deterrent bead according to the invention.

The term "bead" as used herein means a discrete unit such as a particle, particulate, pellet, granule or the like, and the terms "population of beads" and "bead population" each mean a plurality (two or more) of said beads.

The term "gel" as used herein means a three dimensional network or structure formed from a synthetic and/or natural polymer which can absorb and retain a significant amount of water (relative to the amount of polymer) upon exposure to an aqueous environment. Gels are essentially dilute cross-linked systems which may be classified as 'weak' or 'strong' depending on their flow behaviour at steady state (weak—meaning more free flowing or relatively less viscous; strong—meaning less free flowing or relatively more viscous). The term "gelling agent" is construed accordingly as a material which forms, or is capable of forming, a gel upon hydration.

The term "permeable" as used herein means the ability of a coating to allow another substance, particularly water or other solvents, to pass through it. The term "semi-permeable" as used herein means a coating with selective permeability, allowing some substances (such as solvents) to pass through it, whilst not allowing the passage of others (especially solutes). Permeable coatings are taken to include semi-permeable and porous (having interstices or passages that enable liquid to pass though) coatings. By contrast, the term "impermeable" as used herein means a coating which does not allow other substances to pass through it.

The term "pH dependent" as used herein means a parameter which varies with pH (for example, a coating which only dissolves or is only permeable within a particular pH range). By contrast, the term "pH-independent" as used herein means a parameter which does not vary according to pH (for example, a coating material which exhibits similar permeability characteristics irrespective of the pH of it surrounding environment).

The terms "pharmaceutically active ingredient", "active ingredient" and "drug" (used interchangeably) as used herein each means a substance that, when administered to a subject, produces a discernable physiological or pharmacological effect. "Pharmaceutically active ingredient" is taken to include prodrugs which, although not directly active in terms of producing a physiological or pharmacological effect, do give rise to such effects following transformation, within the body of a subject, into an active moiety. Pharmaceutically active ingredients are distinguished from inactive components or excipients which may play a role in the manufacture of, and/or release of active ingredient from, the composition of the invention, but do not elicit any physiological or pharmacological effect when the composition is administered to a subject.

The term "powder" as used herein means a subdivided solid, typically categorised by reference to the size and/or shape of the constituent particles. For the purposes of the present invention substantially all of the particles of a powder pass through a 10 mesh sieve (i.e. having a sieve opening size of 2 mm (2,000 µm).

The term "prodrug" as used herein means a chemical derivative of a drug molecule (a pharmaceutically active ingredient) that undergoes a metabolic transformation within the body of a subject thus releasing the active moiety. The term "ester prodrug" is construed accordingly as an inactive ester form (i.e. —CO—OR; where R is an organic substituent), of a pharmaceutically active ingredient which undergoes transformation, such as hydrolysis, within the body of a subject to release the active drug. The term "carboxamide prodrug" means an inactive form of a pharmaceutically active ingredient bound to an —NRR' moiety via a carbonyl group (i.e. —CO—NRR'; where R and R' are either the same or different and are hydrogen or an organic substituent).

The present invention provides an oral pharmaceutical composition comprising a first population of beads and a second population of beads; said first bead population comprising a pharmaceutically active ingredient susceptible to, or having the potential for, abuse; and said second bead population comprising a gelling agent and a permeable or semi-permeable coating substantially surrounding the gelling agent, but containing no pharmaceutically active ingredient.

The second bead population comprises a coated gelling agent which behaves differently depending on how the composition is handled and/or used. When the gelling agent-containing beads are being processed into a finished dosage form the gelling agent is kept physically separated from the external environment by virtue of the coating. This hinders the ingress of ambient moisture and means that the gelling agent-containing beads remain robust. During the manufacture/processing phase it is important that the gelling agent is not activated (i.e. that it is not caused to swell or gel) so as to avoid handling difficulties, such as clogging equipment.

The composition of the invention is intended to be administered orally. When the composition is administered intact and as intended the various beads disperse along a region of gastrointestinal tract. Water from the surrounding environment is absorbed through the coating of the gelling agent-containing beads which, upon contact with the gelling agent, causes the beads to swell. The beads may swell to the extent that the coating ruptures, thus allowing more rapid ingress of water. This gelling action causes the formation of a viscous mass in and around the vicinity of the beads. However, since the gelling agent is presented in a plurality of beads which spread out within the gastrointestinal tract (as opposed to being a monolithic form, such as a tablet) the gelling agent does not produce a localised mass or lump which may get stuck or cause a blockage. Dispersal of the gelling agent-containing beads in this manner means that the viscous mass produced upon administration of the composition of the invention is not localised to the extent that it might interfere with in vivo release of the drug from the active ingredient-containing beads.

On the other hand, if the composition of the invention is tampered with the gelling agent inhibits or prevents efforts to extract the drug substance. For example, adding the composition to a small volume of water causes the gelling agent to gel as described above. In this case a viscous mass which cannot be syringed is formed. Furthermore, any drug substance dissolved in the water or present as intact beads cannot be decanted or filtered off because of the viscous nature of the mass formed. Any attempt to extract the drug substance that involves crushing the composition followed by the addition of water or some other solvent leads to a similar outcome wherein the active ingredient becomes bound up in a viscous mass that cannot be injected or separated from the drug.

Thus upon ingress of water into the second population of beads the gelling agent is caused to swell forming a gel or viscous mass inhibiting or preventing extraction of the active ingredient from the composition—unless the composition is administered as intended, in which case the action of the gelling agent does not impact release of the drug. There are a number of specific features which highlight the differences between the composition of the invention and prior art compositions. Compositions of the invention exhibit a gelling behaviour when added to water, even in the absence of any tampering i.e. the composition behaves the same whether the gelling agent-containing beads are added to water intact or are crushed first. On the other hand, surprisingly the presence of the gelling agent-containing beads does not have any adverse effect on the release of drug from the composition and its subsequent bioavailability. Certain prior art compositions completely isolate the gelling agent such that it performs no function at all unless the dosage form is tampered with, and specifically, unless an attempt is made to crush the dosage form. In contrast, in the case of the present invention the gelling agent performs an important role in mitigating or preventing extraction of the active ingredient even if the composition is not crushed. Certain prior art compositions are presented in the form of a tablet in which the active ingredient is intimately mixed with the gelling agent. This approach has a number of disadvantages: first, there may be compatibility issues between the drug substance and the gelling agent; secondly, the presence of the gelling agent in such a configuration will inevitably alter the pharmacokinetic characteristics of the composition; and thirdly, the presentation of the gelling agent in the form of a monolithic mass can retard its ability to disperse, thus reducing its effectiveness as an abuse mitigant. Compatibility is not an issue for the present invention because the active pharmaceutical ingredient and the gelling agent are physically removed from each other—being present in separate bead populations. The physical separation of the active ingredient and the gelling agent also means that the release of drug is not impacted by the presence of the gelling agent component. Furthermore, the presentation of the gelling agent in composition of the present invention results in superior performance in terms of the dispersal of the gelling agent, and the formation of a diffuse viscous material, once contacted with a liquid, and in terms of inhibiting the extraction of active ingredient. The gelling action of the composition of the invention produces a diffuse gel of substantially uniform viscosity even in relatively large volumes (e.g. up to about 200 mL). This contrasts with some prior art compositions where a localised gel may be formed, leaving a supernatant portion where the viscosity may remain substantially unchanged—this has the drawback of enabling some of the active ingredient to be extracted from the supernatant.

Preferably the pharmaceutically active ingredient is selected from the group consisting of: alfentanil, allylprodine, alphaprodine, amphetamines (e.g., amphetamine, lisdexamphetamine, methamphetamine, methylenedioxymethamphetamine, dextroamphetamine or methylamphetamine), ephedrine, anileridine, benzodiazepines (e.g., bretazenil, clonazepam, cloxazolam, clorazepate, diazepam, fludiazepam, flutoprazepam, lorazepam, midazolam, nimetazepam, nitrazepam, phenazepam, temazepam or clobazam), benzylmorphine, bezitramide, buprenorphine, butorphanol, carfentanil, clonitazene, codeine, desomorphine, dextromoramide, dezocine, diacetylmorphine, diampromide, diamorphone, dihydrocodeine, dihydromorphine, dimenoxadol, dimepheptanol, dimethylthiambutene, diphenoxylate, dioxaphetyl butyrate, diprenorphine, dipipanone, eptazocine, ethoheptazine, ethylmethylthiambutene, ethylmorphine, etonitazene, etorphine, dihydroetorphine, fentanyl, hydrocodone, hydromorphone, β-hydroxy-3-methylfentanyl, hydroxypethidine, isomethadone, ketobemidone, levo-α-acetylmethadol, levorphanol, levophenacylmorphan, lofentanil, meperidine, meptazinol, metazocine, methadone, methylphenidate, metopon, morphine, myrophine, nalmefene, narceine, nicomorphine, norlevorphanol, normethadone, nalorphine, nalbuphene, normorphine, norpipanone, o-methylnaltrexone, opium, oxycodone, oxymorphone, papaveretum, pentazocine, pethidine, phenadoxone, phenomorphan, phenazocine, phenoperidine, piminodine, piritramide, propheptazine, propranolol, promedol, properidine, propoxyphene, remifentanil, sufentanil, tilidine, and tramadol, or pharmaceutically acceptable salts, solvates, prodrugs, derivatives or active metabolites of any of the foregoing or a mixture thereof.

Particularly preferred active ingredients are those selected from the group consisting of: buprenorphine, butorphanol, codeine, etorphine, fentanyl, hydrocodone, hydromorphone, morphine, oxycodone, or oxymorphone or a pharmaceutically acceptable salt, prodrug, derivative or active metabolite thereof or a mixture thereof. Hydrocodone and pharmaceutically acceptable salts thereof, such as hydrocodone bitartrate, are especially preferred active ingredients because of the abuse potential of these compounds.

Further preferred active ingredients are those selected from the group consisting of 17-(cyclobutylmethyl)-4,14-dihydroxy-6-oxo-morphinan-3-carboxamide and its pharmaceutically acceptable salts.

Other preferred active ingredients are those selected from the group consisting of (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide and its pharmaceutically acceptable salts.

In the case of chiral compounds the active ingredient may be present as a single enantiomer or as a mixture of enantiomers.

The abuse deterrent bead population (i.e. that comprising the gelling agent) of the composition is inactive in the sense that should contain no pharmaceutically active ingredient. The beads comprise a gelling agent core coated with a permeable or semi-permeable coating. In other words, the coating applied to the gelling agent beads represents a physical barrier which is somewhat permeable to water or other solvents. In the case of a pH independent, semipermeable coating the functioning of the coating is not substantially affected by changes in pH.

The distinct and separable nature of individual gelling agent-containing beads means that the gelling agent is not confined in a relatively large, monolithic form—as is the case with a tablet. As a result the gel or viscous mass formed upon exposure of the composition of the invention to water (or some other solvent) is more dispersed or diffuse with substantially consistent viscosity compared that formed in the case of a gelling agent-containing tablet, where the formation of a gel may be relatively localised and limited to a relatively thin layer around the exposed surface(s). The more dispersed, diffuse nature of the gel formed with the present invention arises because of (i) the greater surface area of gelling material exposed in the beads of the invention compared to a monolithic tablet; and (ii) the readily accessible nature of the gelling agent. The permeable or semipermeable nature of the coating means that the gelling agent-containing beads will absorb at least some water irrespective of whether or not the composition has been tampered with. The formation of a gel in and around the composition helps to frustrate attempts to extract the active ingredient from the composition, whether in crushed form or intact. This contrasts with some prior art compositions in which a gelling component is only exposed when the dosage form is crushed or tampered with in some way.

Another advantage of the composition of the invention is the distinct and separable nature of the active ingredient beads, on one hand, and the gelling agent beads, on the other. This means that there is no direct physical interaction between the pharmaceutically active ingredient and the gelling agent. Thus any chemical incompatibility between the two is mitigated. Furthermore, this separation of the active ingredient and the gelling agent means that there is no detrimental effect on the release and/or bioavailability of the active ingredient—an issue which can arise where the active ingredient and a gelling agent are present in an intimate mixture.

Gelling agents suitable for use in the present invention include gel forming polymeric materials which swell upon contact with or absorption of a solvent, such as water, alcohol or some aqueous liquid, thus forming a viscous substance. The gel formed upon hydration of the gel agent may be a strong gel or a weak gel. The formation of such a gel or viscous mass in the vicinity of or around the first (drug-containing) bead population makes it difficult, if not impossible, to separate the active ingredient-containing beads or to extract the drug substance from the composition, particularly where the active ingredient is present in the form of controlled release beads. Gelling agents suitable for use in the composition of the present invention include hydrophilic cellulosic polymers, polyethylene oxide of various molecular weights (for example having an average molecule weight in the range of from about 100,000 to about 10,000,000 Daltons, preferably within the range of from 750,000 to 7,500,000 Daltons), carbomers (polymers of acrylic acid cross-linked with polyalkenyl ethers of sugars or polyalcohols) of various grades; gums such as xanthan gum, guar gum, locust bean gum, gellan gum and glucomannan; and the like. Preferably the gelling agent comprises a polymer selected from the group consisting of hydroxypropyl cellulose, methylcellulose, hydroxypropylmethyl cellulose, polyethylene oxide, sodium carboxymethyl cellulose, sodium alginate and carrageenan.

Polyethylene oxide has been found to be particularly useful in the composition of the invention by virtue of its ability to gel quickly and to form a diffuse viscous mass inhibiting extraction of the pharmaceutically active ingredient. Preferably the PEO used has an average molecular weight of from 750,000 to 7,500,000, more preferably from about 1,000,000 to about 6,500,000.

The gelling agent may be granulated to produce granules which can then be coated. Alternatively, the gelling agent-containing beads may be built up on a core/substrate using powder-dosing or spray application techniques known in the art. The core may be an "inert" core, in the sense that its sole function is to act a substrate upon which to build the beads (for example nonpareils or sugar spheres, microcrystalline cellulose spheres and the like). Alternatively the core may be made of a material which serves an additional purpose as well as acting as a substrate (for example the core may be made of a buffering agent such as tartaric acid).

Where an inert core is used as a substrate for the gelling agent-containing-beads the gelling agent may be applied to the inert core in any suitable form. For example it may be applied as a powder or as a suspension or solution of the gelling agent in a suitable medium/solvent. Preferably the gelling agent is incorporated into the gelling agent-containing beads in the form of a powder.

Typically the gelling agent-containing beads may be built up by applying the gelling agent to the core for subsequent coating. The use of an inert core in the gelling agent-containing beads is preferred when a similar approach is used for producing the active ingredient-containing beads (i.e. applying a layer of active ingredient to an inert core)—this is because it may be difficult to match the shape and size of gelling agent-containing beads produced by a granulation approach to the shape and size of active ingredient-containing beads produced using the inert core approach. Typically substrate/nonpareil seeds having an average diameter of 0.5-0.6 mm, 0.6-0.71 mm or 0.71-0.85 mm may be used. A visible distinction between the active ingredient beads and the gelling agent beads that would enable the different types of beads to be distinguished and separated should be avoided.

In order to further enhance hydration and gelling it may be advantageous for the gelling agent to be present in particulate form (i.e. as discrete particles, such as a powder), as opposed to being present as a film. When the gelling agent in the second bead population is present in the form of particles the gelling agent applied to a substrate, the beads may further comprise a binder to aid adhesion of the gelling agent to the substrate. The binder may also reduce possible hydration of the gelling agent during the manufacturing process, thus helping to maintain the discrete particulate nature of the gelling agent and the hydration action of the final beads. The binder may suitably be selected from the group consisting of disaccharides, such as sucrose and lactose; polysaccharides, such as starch and microcrystalline cellulose; sugar alcohols, such as sorbitol and xylitol. Preferably the binder is selected from the group consisting of hydroxypropyl cellulose, hydroxypropyl methyl cellulose and polyvinyl pyrrolidone. A particularly preferred binder is povidone (polyvinyl pyrrolidone), such as that sold under the trade mark Kollidon (BASF SE) for example "Kollidon K30". The binder, if present, may be used in any amount that successfully binds the gelling agent to the substrate. When used, the binder is typically present in an amount of from 1 to 25% of the dry weight of gelling agent present, and preferably in an amount of from 10 to 15% of the dry weight of gelling agent. When a binder is used it is preferably applied to the substrate as a solution simultaneously with application of the gelling agent powder. Preferably the solvent used to form the binder solution comprises little or no water, thus minimising hydration or dissolution of the gelling agent. Suitable solvent systems for use in application of the binder include isopropyl alcohol and isopropyl alcohol/water mixtures having a water content of 30% (by volume) of less. A preferred binder solution is povidone (from about 1 to about 10% w/w) in a 5:1 isopropyl alcohol/water mixture.

Preferably the gelling agent-containing beads comprise an inert core, such as sugar spheres, supporting a gelling agent, such as polyethylene oxide (PEO), coated with a semipermeable coating, such as an ammonio methacrylate copolymer or a methacrylic acid copolymer. PEO may hydrate and disperse more quickly when in the form of aggregated particles as opposed to when it is formed as a film or compressed into a tablet. Furthermore, particulate PEO may facilitate the formation of a dispersed or diffuse gel. Accordingly, the polyethylene oxide is preferably present as a layer of PEO particles between the inert core and the semipermeable coating. One embodiment of such a gelling agent-containing bead is shown schematically in FIG. 1. The gelling agent-containing bead (1) comprises a substrate (2) preferably made of an inert material the sole function of which is to act as a foundation to support the other elements of the bead. The gelling agent (3) is applied to the substrate (2), preferably in particulate form (e.g. a polyethylene oxide powder). This may be achieved by applying a powder of the gelling agent, on to the substrate (2). If a binder is being used it may be applied in the form of a solution (in a suitable solvent) simultaneously with the application of the gelling agent. The permeable or semi-permeable coating (4) is then applied over the gelling agent layer (3).

Preferably an oral pharmaceutical composition of the invention comprising a second bead population wherein the gelling is particulate polyethylene oxide and wherein the coating, comprises an ammonio methacrylate copolymer and/or a methacrylic acid copolymer, further comprises povidone. The povidone acts as a binder further facilitating and enhancing the gelling action of the beads.

The gelling agent may suitably be present in any amount that causes the composition to gel upon exposure to water to the extent that the viscosity of the composition mixed with a small amount of water (for example 0.5 to 10 mL at 20° C.) prevents the mixture from being drawn up into a syringe (for example an 18 gauge (1.270 mm diameter) needle). Preferably the gelling agent is present in an amount which does not cause any handling problems during manufacture of the composition (such as clogging of coating, encapsulation or tableting equipment). Where the composition is presented in a capsule the gelling agent may be present in amount of at least 15% (w/w) of the combined dry weight of active ingredient(s) and excipients present (in other words 15% (w/w) of the overall dry weight of composition), or at least 20 mg, preferably at least 30 mg per capsule.

The coating applied to the gelling agent is a permeable or semi-permeable coating. Suitable permeable and semi-permeable coating materials are known in the art. These include for example cellulosic polymers, such as cellulose acetates, cellulose alkanylates and cellulose acrylates; polyamides; polyurethanes; sulfonated polystyrenes; ammonio methacrylate copolymers such as poly(ethyl acrylate-co-methyl methacrylate-co-trimethylammonioethyl methacrylate chloride) 1:2:0.1 (for example those sold under the trade name Eurdgit® RS (Evonik Industries AG); and methacrylic acid copolymers such as poly(methacrylic acid-co-ethyl acrylate) 1:1 (those sold under the trade name (Eudragit® L (Evonik Industries AG)). Preferably the coating comprises an ammonio methacrylate copolymer or a methacrylic acid copolymer or a mixture of the foregoing.

The level of coating applied to the beads can be characterised in terms of weight gain (i.e. the weight of material applied to the uncoated beads) or in terms of coating thickness. From a manufacturing perspective coating to a specified weight gain is more practical as this can be more readily determined and controlled in-process.

When expressed in terms of weight gain, the coating may be characterised in terms of the weight of polymer(s) only applied, or in terms of the weight of polymer solution/suspension (which may contain excipients such as pore formers, anti-adherents etc in addition to the polymer(s)). The coating may suitably be present in an amount of about 5% to about 50% polymer weight gain (i.e. polymer weight added expressed as a percent of the weight of uncoated beads; excluding weight of any excipients added with the polymer). When the coating comprises an ammonio methacrylate copolymer or a methacrylic acid copolymer, or a mixture thereof, the coating is preferably applied to a polymer weight gain of from about 7.5% to about 25%.

The coating level may also be characterised in terms of coating thickness. However, as will be appreciated by the skilled person the uncoated beads are not perfect spheres and coating materials are not applied with perfect uniformity across the entire surface of all beads. Therefore, coating thickness may vary somewhat across different areas of any given bead and also from one bead to the next. Any coating thickness which forms robust, separable beads and which facilitates ingress of water and hydration of the gelling agent will suffice for the purposes of the invention. Preferably the coating will have a thickness from about 1 to about 100 μm (microns). When the coating comprises an ammonio methacrylate copolymer or a methacrylic acid copolymer the coating is preferably applied to a thickness of about 10 to about 50 μm.

As will be appreciated by the skilled person, the coating may further comprise excipients designed to control the permeability of the coating and/or the processing characteristics of the coating. For example, the coating may further comprise one or more excipients selected from the group consisting of pore formers, plasticisers, lubricants, glidants and anti-adherent agents and the like.

The coating may comprise a water soluble pore former to aid permeability and thus facilitate hydration of the gelling agent. Suitable pore forming agents include hydroxypropyl methyl cellulose or other cellulosic derivatives, polyvinyl alcohol (PVA), polyethylene glycol (PEG), PVA-PEG copolymers, copovidone and the like. Mixtures of two or more pore formers may be employed. The use of a pore former may be particularly advantageous if a pH dependent coating is used. Some pH dependent coatings, such as enteric coatings, typically remain intact—preventing ingress of water—until exposed to a particular pH. In such a scenario the lack of permeability may be addressed by the addition of a pore former, thus imparting a suitable degree of permeability to an otherwise impermeable coating. If present in the composition the pore former may typically be used in an amount of from 1 to 20% w/w of the dry weight of coating polymer/material employed.

Where the coating comprises a plasticiser suitable plasticisers include for example phthalates, such as alkyl or dialkyl phthalates including dimethyl phthalate, ethyl phthalate, diethyl phthalate, and dibutyl phthalate; citrates including triethyl citrate and acetyl triethyl citrate; and other plasticisers known in the art such as dibutyl sebacate, triacetin and the like. When the coating comprises an ammonio methacrylate copolymer or a methacrylic acid copolymer or a mixture thereof particularly preferred plasticisers are those selected from the group consisting of diethyl phthalate, dibutyl phthalate, triethyl citrate and dibutyl sebacate. When present, the plasticiser may typically be used in an amount of from about 10 to about 30% (w/w) of the polymer applied.

The nature of the coating on the gelling agent-containing beads is such that the composition of the invention is adapted to expose the gelling agent to water (or some other liquid from its surrounding environment) in a controlled fashion when the composition is used intact and as intended.

Without wishing to be bound by any particular theory it is thought that when the intact second bead population is exposed to water (or some other liquid) the permeable or semi-permeable nature of the coating enables some water to pass through the coating, thus initiating hydration of the gelling agent. When the resultant swelling of the gelling agent can no longer be contained by the coating, the coating cracks or fractures facilitating further hydration. Upon further hydration the coating may breakdown to the extent that some of the gelling agent is released into the nearby vicinity. It is thought that dispersal of the gelling agent in this manner leads to the formation of a more diffuse, substantially uniform, gel compared to the situation where a gelling agent is presented in the form of a compacted mass, such as in a tablet. If the composition is tampered with exposure of the gelling agent to water may occur in a more rapid and less controlled manner. In either case the presence of the gelling agent-containing beads functions to deter or prevent extraction of the active ingredient in a form that may be abused.

When the composition (either intact or crushed) is mixed with a relatively small volume of water a viscous mass is formed which makes it extremely difficult, if not impossible, for any of the pharmaceutically active ingredient to be drawn up into a syringe. It is particularly advantageous for the composition to comprise a quantity of gelling agent which takes up substantially all of the volume of water required to dissolve and extract the amount of active ingredient present. For example, the composition may comprise a quantity of gelling agent which will take up or absorb the minimum volume of water required to dissolve substantially all of the active ingredient present in the composition. In this way no supernatant will remain above the viscous mass (a strong gel) formed upon gelling of the gelling agent. In other words, there will be no residual solution of the drug which could be filtered or decanted off in order to separate it from the viscous material. Preferably, the composition comprises a quantity of gelling agent sufficient to ensure that when the composition is mixed (e.g. stirred or shaken at 20° C. and then left to sit for 10 min) with from about 1 to about 10 mL of water no supernatant is formed i.e. substantially the entire volume of water is absorbed by the gelling agent in the formation of a viscous mass leaving no residual, separable active ingredient solution.

On the other hand, attempting to extract the active ingredient by mixing the composition (either intact or crushed) with a relatively large volume of water, with a view to dissolving the active ingredient and separating it from the remaining constituents by decanting or filtration, produces a larger, more dispersed viscous mass (a weak gel), entrapping at least some the drug (for example undissolved drug which may still be present as intact drug-containing beads—particularly if there is a controlled release (CR) component in the composition). Any given amount of gelling agent may have a finite capacity to take up, hold or absorb water. If a sufficiently large volume of water is used and this threshold is passed, then a supernatant may form. If a composition of the invention is mixed with a relatively large volume of water, exceeding the capacity of the quantity of gelling agent present, and if the composition comprises an immediate release (IR) component, then at least some of the IR portion of active ingredient may be dissolved in the supernatant. However, even in a scenario where the supernatant may be separable from the viscous material, the composition can be adapted such that the active ingredient solution thus recovered will be much too dilute and of such a low strength (in terms of drug concentration) for it to produce a "high" were it to be injected. Accordingly, the invention provides a dosage form comprising a first population of beads and a second population of beads; said first bead population comprising a pharmaceutically active ingredient susceptible to, or having the potential for, abuse; and said second bead population (containing no pharmaceutically active ingredient) comprising a gelling agent and a permeable or semipermeable coating; wherein, said first bead population and said second bead population are physically separable, but visually indistinguishable to the naked eye; and wherein less than about 25% (w/w) of the active pharmaceutically active ingredient is extracted from the composition after placing the dosage form in 100 mL of water for 30 min at 20° C.

In one preferred embodiment the pharmaceutically active ingredient contained in the first population of beads is hydrocodone, or a pharmaceutically acceptable salt thereof, and the second population of beads comprises polyethylene oxide, povidone (polyvinyl pyrrolidone) and a polymer selected from the group consisting of an ammonio methacrylate copolymer, a methacrylic acid copolymer and a mixture thereof.

The present invention provides an oral pharmaceutical composition comprising a first population of beads and a second population of beads; said first bead population comprising a pharmaceutically active ingredient susceptible to, or having the potential for, abuse; and said second bead population comprising a gelling agent and a permeable or semi-permeable coating, but containing no pharmaceutically active ingredient; wherein, said first bead population and said second bead population are physically separable, but visually indistinguishable to the naked eye. In other words, an oral pharmaceutical composition comprises at least one active ingredient-containing component (the first bead population as described above) and a component devoid of any pharmaceutically active ingredient (the second, gelling agent-containing, bead population as described above). However, in order to manipulate the amount of drug present and the release profile, the composition may contain multiple active ingredient containing constituents.

For example, the active ingredient-containing component may comprise more than one population of active ingredient containing beads, with each of such populations being adapted to release the drug in a different manner or at a different rate. The composition may comprise an immediate release active ingredient-containing population of beads which release the drug upon administration, without any delay, and a controlled release active ingredient-containing population of beads which is adapted to release the drug in a manner which is not immediate (e.g. delayed release, sustained release or some other form of modified or controlled release). The controlled or sustained release component may be modified so as to provide a lag or delay following administration before the drug is released. Such a lag or delay may be achieved by coating the active ingredient-containing beads with a controlled release coating known to the skilled person. In this manner two or more pulses of drug release may be incorporated into the composition, thus providing flexibility in designing an appropriate overall release profile.

An oral pharmaceutical composition of the invention may comprise immediate release active ingredient-containing beads, controlled release active ingredient-containing beads, and gelling agent-containing beads; wherein said immediate release and said controlled release beads comprise a pharmaceutically active ingredient susceptible to, or having the potential for, abuse; and said gelling agent-containing beads comprise a gelling agent, but containing no pharmaceutically active ingredient; wherein, the various bead populations are each physically separable, but visually indistinguishable to the naked eye.

A multiparticulate modified release hydrocodone bitartrate composition is described in US 2006-0240105 A1 (("the '105 publication"—the entire contents of which are incorporated herein by reference) see in particular Example 3; paragraphs [0099] to [0106], including Tables 6 to 11). An oral morphine multiparticulate composition is disclosed U.S. Pat. No. 6,066,339 (("the '339 patent"—the entire contents of which are incorporated herein by reference) see in particular Examples 1 to 6; columns 7 to 15, including the tables therein). Multiparticulate modified release compositions are disclosed in U.S. Pat. No. 6,228,398 (("the '398 patent"—the entire contents of which are incorporated herein by reference) see in particular Examples 1 and 2 and the accompanying tables and figure). A composition of the present invention may be produced by combining a gelling agent-containing population of beads having a semi-permeable coating to the multiparticulate modified release composition of the '105 publication, the '399 patent or the '398 patent.

Alternatively, immediate release and controlled release of active ingredient may be combined in a single bead population. This may be achieved by providing a drug containing core coated with a controlled release coating (the controlled release component) which is in turn coated with a layer of drug (the immediate release component). Upon administration the outer drug layer is released immediately whilst release of drug from the coated core is modified according to the characteristics of the controlled release coating. Again, in this manner two or more pulses of active ingredient may be incorporated into the composition, thus providing flexibility in designing an appropriate overall drug release profile.

The composition of the invention may comprise one or more pharmaceutically active ingredients. Where the composition comprises a plurality of active ingredients said active ingredients may be present in the same population or separate populations of active ingredient-containing beads.

The composition of the invention comprising pharmaceutically active ingredient-containing beads and coated gelling agent beads as described above may be processed into a finished dosage form, for example by filling a mixture of the various bead populations in the desired proportions into a capsule. The beads are released from the capsule upon administration to a subject. Depending on the dosage strength and volume of the composition to be used the capsule size may range for example from a size 5 capsule to a size 000. In terms of patient acceptability it is preferable that the composition be filled into a capsule no bigger than a size 0E (elongated size 0) or a size 00. Alternatively, the composition may be processed into tablet form by compressing the blended beads into tablets. Where the composition is to be incorporated into a tablet the various beads may be compressed together with a binder and/or hardening agent commonly employed in tableting such as microcrystalline cellulose (e.g. that sold under the trade mark Avicel® (FMC Corporation)) or a co-crystallised powder of maltodextrin and sucrose (e.g. that sold under the trade mark Di-Pac® (American Sugar Refining, Inc)). Upon administration to a subject the tablet disintegrates to release the beads contained therein into the GI tract, thus exposing them to GI fluids.

Where the composition comprises hydrocodone or a pharmaceutically acceptable salt thereof, such as hydrocodone bitartrate, said active ingredient is preferably present in an amount from 5 to 250 mg per unit dosage form.

In one embodiment an oral pharmaceutical composition comprises a first population of beads and a second population of beads; said first bead population comprising hydrocodone or a pharmaceutically acceptable salt thereof; and said second bead population, free from pharmaceutically active ingredient(s), comprising polyethylene oxide, povidone and a polymer selected from an ammonio methacrylate compolymer, a methacrylic acid copolymer or a mixture thereof. The hydrocodone or pharmaceutically acceptable salt may be the sole pharmaceutically active ingredient present in the composition. Preferably the first bead population comprises hydrocodone bitartrate in an amount from 5 to 250 mg.

In one embodiment an oral pharmaceutical composition comprises a population of immediate release hydrocodone bitartrate beads, a population of controlled release hydrocodone bitartrate beads and a population of gelling agent-containing beads; said gelling agent-containing beads comprising polyethylene oxide, povidone and a permeable or semi-permeable coating material selected from an ammonio methacrylate compolymer, a methacrylic acid copolymer or a mixture thereof, but containing no pharmaceutically active ingredient. Preferably the immediate release beads contain from 1 to 75% w/w of the total amount of hydrocodone bitartrate in the composition and the controlled release beads contain the remainder i.e. the controlled release beads contain from 25 to 99% w/w of the total amount of hydrocodone bitartrate in the composition.

The invention provides a dosage form comprising a composition according as described above wherein the gelling agent is present in each individual dosing unit (e.g. each capsule or tablet) in an amount sufficient to form an abuse deterring gel when the dosage form is mixed with or added to 1 to 100 mL of water. Typically the gelling agent is present in each individual dosing unit in an amount of at least about 20 mg (per unit), preferably in an amount of at least 30 mg (per unit). The upper limit of the amount of gelling agent that may be used is determined by a combination of the size of the active ingredient-containing beads and the size of the dosage form (i.e. capsule or tablet). Whilst in general it is preferable for the composition to comprise as much gelling agent as possible, this is balanced by the need for the gelling agent-containing beads to match the active ingredient beads in size and appearance so as to prevent separation of the different bead populations. Furthermore, the overall size of the capsule or tablet into which the composition is incorporated will place a limit on the amount of gelling agent-containing beads that can be used. Preferably the gelling agent is present in each individual dosing unit in an amount from 20 to 500 mg (per unit). Preferably the gelling agent is present in an amount sufficient to provide a gelling agent/active ingredient ratio for the composition of from 1:10 to 10:1.

Gelling agent-containing beads for use in the present invention may be prepared according to the following general method:

(a) The gelling agent (together with the binder, if any) is applied to a core using a fluid bed processor, to form uncoated gelling agent beads;

(b) The coating material (together with any glidant and other excipients, if any) is then applied to the uncoated beads obtained from the previous step using a fluid be processor, to form coated gelling agent beads having a coating of the desired weight gain or thickness; and (c) The coated beads obtained from the previous step are then dried, typically for a period of about 12 to 24 hours and a temperature of about 30 to 50° C., to form finished gelling agent-containing beads.

The finished beads may optionally be screened to separate beads of a desired particle size (diameter).

The gelling agent-containing beads (which contain no pharmaceutically active ingredient) may be blended with active ingredient-containing beads to form a blend which may be filled into capsules or compressed into tablets. Alternatively, in the case of a capsule presentation, gelling agent-containing beads of the invention may be added to the capsule separately, either before or after other components of the dosage form. Active ingredient-containing beads may be prepared according to processes known in the art, such as those disclosed in U.S. Pat. No. 6,066,339, U.S. Pat. No. 6,228,398 or US 2006-0240105 A1 for example (the entire contents of each of which are incorporated herein by reference).

Depending on the dosage strength, the dosage form and the relative proportions of the different bead populations present, the amounts of the various constituents in the composition may vary. Some exemplary formulations for abuse resistant compositions according to the invention, indicating typical ranges for the amount of each component present, are shown in Table (i).

TABLE (i)

Abuse resistant compositions.

| Material | Range (% w/w) |
| --- | --- |
| Pharmaceutically active ingredient(s) | 1.0-20.0 |
| Bead substrate (e.g. sugar spheres) | 35.0-60.0 |
| Controlled release polymer(s) | 2.5-25.0 |
| Glidant(s)/anti-adherant(s) | 0.5-7.5 |
| Gelling agent(s) | 15.0-45.0 |
| Binder(s) | 1.0-5.0 |

Further details of how to prepare compositions according to the invention are set out in the Examples below.

The present invention also relates to methods of treatment based on the abuse resistant oral pharmaceutical compositions described above. Accordingly, the invention provides a method of treating a subject in need of treatment with a pharmaceutically active ingredient susceptible to, or having the potential for, abuse comprising the step of administering to said subject an effective amount of an oral pharmaceutical composition comprising a first population of beads and a second population of beads; said first bead population comprising the pharmaceutically active ingredient susceptible to, or having the potential for, abuse; and said second bead population comprising a gelling agent and a permeable or semi-permeable coating, but containing substantially no pharmaceutically active ingredient.

A preferred method of the invention is a method for the treatment of pain comprising administering to a subject in need thereof a composition as described above wherein said first population of beads comprises an analgesically effective amount of a pharmaceutically active ingredient selected from the group consisting of hydrocodone, hydrocodone bitartrate, 17-(cyclobutylmethyl)-4,14-dihydroxy-6-oxo-morphinan-3-carboxamide, (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide and pharmaceutically acceptable salts of the foregoing. Preferably where the pharmaceutically active ingredient used in the foregoing method is hydrocodone or a pharmaceutically acceptable salt thereof, said active ingredient is present in an amount of between 5 and 250 mg per unit dosage form. In a particularly preferred embodiment, the method of the invention comprises administering a composition comprising between 5 and 250 mg of hydrocodone or a pharmaceutically acceptable salt thereof, wherein said hydrocodone or said pharmaceutically acceptable salt thereof is the sole pharmaceutically active ingredient present in the composition.

EXAMPLES

The source of various materials and equipment is indicated throughout the Examples. Where a source is not indicated the material or equipment would be readily available to the skilled person.

In the Examples that follow: "EP" means European Pharmacopeia; "NF" means National Formulary; and "USP" means US Pharmacopeia.

Example 1

1.1 Polyethylene Oxide Beads

Abuse deterrent beads for use in compositions according to the invention were prepared using the materials set out in Table 1.1 below.

TABLE 1.1

Composition of gelling agent-containing, abuse deterrent beads.

| Material (Type/Grade) | Amount (mg/g) | Amount (% (w/w)) |
| --- | --- | --- |
| Polyethylene oxide (Polyox ® WSR[1] coagulant LEO, NF) | 443.9 | 44.39 |
| Povidone (K30[2], USP) | 45.5 | 4.55 |
| Sugar spheres (30/35 mesh, NF) | 317.0 | 31.70 |
| Eudragit ® RS (ammonio methacrylate copolymer Type B[3], NF EP) | 96.8 | 9.68 |
| Silicon dioxide (Syloid ® 244[4] FP, NF) | 48.4 | 4.84 |
| Talc (USP EP) | 48.4 | 4.84 |
| Total | 1,000.0 | 100.00 |

[1]The Dow Chemical Company - Midland, MI, USA;
[2]Sigma-aldrich Corp. - St. Louis, MO, USA;
[3]Evonik Industries AG, Essen Germany;
[4]WR Grace & Co. - Columbia, MD, USA.

The abuse deterrent beads were manufactured as follows:
A binder solution containing the povidone dissolved in isopropyl alcohol and water* (20% by weight $H_2O$ in IPA) was prepared.
The ammonio methacrylate copolymer was dissolved in a mixture of isopropyl alcohol, acetone and water (78.0%/16.6%/5.4% by weight i.e. IPA:acetone:ratio of 14.44:3.04:1)) to form a 5.5% w/w polymer solution.
A glidant blend was prepared by bag blending the silicon dioxide and talc.
The binder solution and polyethylene oxide (powder; having an average molecular weight of approx. 5,000,000) were then simultaneously applied onto 30/35-mesh sugar spheres using a Vector Granurex GX-40 rotor processor (Freund-Vector Corp.—Marion, Iowa, USA). The Granurex process parameters used were as follows—slit air temperature: 25-42° C.; slit air flow: 10-30 cfm; rotor speed: 180-205 rpm; binder solution spray rate: 13-56 g/min; PEO powder feed rate: approx. 6-48 g/min.
The coating suspension and glidant blend were then applied to the polyethylene oxide layered sugar spheres forming abuse deterrent beads using a Vector Granurex GX-40 rotor processor (Freund-Vector Corp.—Marion, Iowa, USA). The process parameters for applying the coating were as follows—slit air temperature: 42° C.; slit air flow: 30 cfm; rotor speed: 250 rpm; coating solution spray rate; powder feed rate: 2.0 g/min.
The abuse deterrent beads were dried in a temperature and humidity-controlled oven (flatbed tray oven) for 20 hours at 40° C./50% RH (relative humidity) to reduce residual solvent and stabilize any moisture content.
After drying, the beads were collected and screened using a Russell Finex sieve shaker (Russell Finex Limited—Fletham, Middlesex, United Kingdom) to separate oversize material (retained on a 16-mesh sieve) and fines (through a 40-mesh sieve), if any, formed during the process.
(* The solvents mentioned are driven off during the manufacturing process and/or during drying and are not incorporated into the end product to any significant degree.)
(** The solution spray rate and the powder feed rate were ramped up in tandem as the batch progressed.)

1.2 Hydrocodone Bitartrate Immediate Release Beads

Hydrocodone bitartrate immediate release (IR) beads having the composition set out in Table 1.2 were prepared as described below.

TABLE 1.2

Composition of hydrocodone bitartrate immediate release beads.

| Material (Type/Grade) | Amount (mg/g) | Amount (% (w/w)) |
| --- | --- | --- |
| Hydrocodone bitartrate (USP)[5] | 200.0 | 20.00 |
| Sugar spheres (30/35 mesh, NF) | 683.3 | 68.33 |
| Silicon dioxide (Syloid ® 244 FP, NF) | 66.7 | 6.67 |
| Hypromellose 2910 (6 cPs, USP) | 50.0 | 5.00 |
| Total | 1,000.0 | 100.00 |

[5]Noramco, Inc - Athens, GA, USA

The hydrocodone bitartrate IR beads were manufactured as follows:
A solution containing 1.5% w/w hypromellose and 6.0% w/w hydrocodone bitartrate dissolved in water was prepared.
2.0% w/w silicon dioxide was added to the solution formed in the previous step and mixed to form an immediate release coating solution.

The IR coating solution was then applied onto 30/35-mesh sugar spheres using a Glatt® GPCG fluid bed system (Glatt air Techniques, Inc—Ramsey, N.J., USA) equipped a Wurster insert.

After application of the active to the sugar spheres, the resultant IR beads were dried for approximately 10 minutes in the fluid bed and cooled before discharge.

The discharged beads were then screened using a Russell Finex sieve shaker to separate oversize (retained on a 20-mesh sieve) and fines (through a 35-mesh sieve), if any, formed during the process.

The screened beads produced according to the above process were either used as IR beads or processed further to produce SR beads as set out below.

1.3 Hydrocodone Bitartrate Controlled Release Beads—1

As described below hydrocodone bitartrate IR beads as described above were coated with a pH independent polymer coating to produce controlled release (CR) beads having the composition set out in Table 1.3.

A coating suspension was prepared as follows:

The ammonio methacrylate copolymer type B (Eudragit® RS) was dissolved in a mixture of isopropyl alcohol, acetone, and water (78.0:16.6:5.4).

Talc and silicon dioxide (0.83% w/w in each case) were added to the solution from the previous step as anti-adherents to prevent agglomeration of the beads during coating.

The CR coating suspension was applied onto immediate release beads as prepared above in section 1.2 using a Glatt GPCG fluid bed system equipped with a Wurster insert.

TABLE 1.3

Composition of hydrocodone bitartrate controlled release beads.

| Material (Type/Grade) | Amount (mg/g) | Amount (% (w/w)) |
|---|---|---|
| Hydrocodone bitartrate (USP) | 179.0 | 17.90 |
| Sugar spheres (30/35 mesh, NF) | 611.6 | 61.16 |
| Hypromellose 2910 (6 cPs, USP) | 44.8 | 4.48 |
| Eudragit ® RS (ammonio methacrylate copolymer Type B, NF EP) | 80.6 | 8.06 |
| Silicon dioxide (Syloid ® 244 FP, NF) | 71.8 | 7.18 |
| Talc (USP EP) | 12.2 | 1.22 |
| Total | 1,000.0 | 100.00 |

Coating was performed until a polymer weight gain of 9% was achieved. After the target weight was applied, the CR beads were dried for approximately 10 minutes in the fluid bed and cooled before discharge. Coated beads were then dried in a temperature and humidity-controlled oven for 20 hours at 40° C./50% RH. After drying, the beads were collected and screened using a Russell Finex sieve shaker to separate oversize (retained on a 20-mesh sieve) and fines (through a 35-mesh sieve), if any, formed during the process.

1.4 Hydrocodone Bitartrate Controlled Release Beads—2

Controlled release beads having the composition set out in Table 1.4 were prepared.

The coating suspension comprising a pH dependent polymer was prepared as follows:

Methacrylic acid copolymer Type A (Eudragit® L) (6.25% w/w) and triethyl citrate (12.5% w/w) were dissolved in a mixture of isopropyl alcohol, acetone and water (78.0:16.6:5.4).

Talc and silicon dioxide (0.94% w/w in each case) were added to the solution from the previous step as anti-adherents to prevent agglomeration of the beads during coating.

The coating suspension was applied to CR beads described above in section 1.3 to a polymer weight gain of 20% using a similar procedure to that described in section 1.3.

TABLE 1.4

Alternate composition of hydrocodone bitartrate sustained release beads.

| Material (Type/Grade) | Amount (mg/g) | Amount (% (w/w)) |
|---|---|---|
| Hydrocodone bitartrate (USP) | 137.7 | 13.77 |
| Sugar spheres (30/35 mesh, NF) | 470.4 | 47.04 |
| Hypromellose 2910 (6 cPs, USP) | 34.4 | 3.44 |
| Eudragit ® RS (ammonio methacrylate copolymer Type B, NF EP) | 62.0 | 6.20 |
| Silicon dioxide (Syloid ® 244 FP, NF) | 78.4 | 7.84 |
| Talc (USP EP) | 32.5 | 3.25 |
| Eudragit ® L (methacrylic acid copolymer Type A[6], NF EP) | 153.8 | 15.38 |
| Triethyl citrate (NF) | 30.8 | 3.08 |
| Total | 1,000.0 | 100.00 |

[6]Evonik Industries AG, Essen Germany

The hydrocodone IR and CR beads may be mixed in different proportions and filled into capsules to provide dosage forms having different strengths and release profiles.

Example 2

A composition of the invention, Composition 1 (summarized in Table 2.1 below), was prepared by blending IR beads as described in section 1.2 and CR beads as described in section 1.3, in a ratio of 20:80 (IR:CR) based on hydrocodone bitartrate content and filling the resultant blend into size 0 hard gelatin capsules along with 75 mg of PEO beads as described in section 1.1 to produce compositions having a strength of 20 mg/capsule.

TABLE 2.1

Hydrocodone bitartrate Composition 1 (per capsule).

| Material (Type/Grade) | Composition 1 Amount (mg) |
|---|---|
| Hydrocodone bitartrate (USP) | 20.0 |
| Sugar spheres (30/35 mesh, NF) | 92.1 |
| Hypromellose 2910 (6 cPs, USP) | 5.0 |
| Eudragit ® RS (ammonio methacrylate copolymer Type B, NF EP) | 14.5 |
| Silicon dioxide (Syloid ® 244 FP, NF) | 11.4 |
| Talc (USP EP) | 4.7 |
| Polyethylene oxide (Polyox ® WSR coagulant LEO, NF) | 33.3 |
| Povidone (K30, USP) | 3.4 |
| Total | 184.4 |

A comparator composition, Composition 2 (summarized in Table 2.2), which was essentially the same as Composition 1, but with no gelling agent-containing bead component, was prepared by blending IR beads as described in section 1.2 and CR beads as described in section 1.3 in a ratio of 20:80 (IR:CR) based on active ingredient content and filling the resultant blend into size 0 hard gelatin capsules to produce compositions having a strength of 20 mg/capsule.

TABLE 2.2

Comparator Composition 2 (per capsule)

| Material (Type/Grade) | Composition 2 (Control) Amount (mg) |
|---|---|
| Hydrocodone bitartrate (USP) | 20.00 |
| Sugar spheres (30/35 mesh, NF) | 68.34 |
| Hypromellose 2910 (6 cPs, USP) | 5.00 |
| Eudragit ® RS (ammonio methacrylate copolymer Type B, NF EP) | 7.20 |
| Silicon dioxide (Syloid ® 244 FP, NF) | 7.76 |
| Talc (USP EP) | 1.08 |
| Total | 109.38 |

Example 3

A composition of the invention, Composition 3 (summarized in Table 3.1 below) was prepared by blending IR beads as described in section 1.2 and CR beads as described in section 1.4 in a ratio of 20:80 (IR:CR) based on active ingredient content and filling the resultant blend into size 0 hard gelatin capsules along with 75 mg of PEO beads as described in section 1.1 to produce compositions having a strength of 20 mg/capsule.

TABLE 3.1

Hydrocodone bitartrate Composition 3 (per capsule).

| Material (Type/Grade) | Composition 3 Amount (mg) |
|---|---|
| Hydrocodone bitartrate (USP) | 20.0 |
| Sugar spheres (30/35 mesh, NF) | 92.1 |
| Hypromellose 2910 (6 cPs, USP) | 5.0 |
| Eudragit ® RS (ammonio methacrylate copolymer Type B, NF EP) | 14.5 |
| Silicon dioxide (Syloid ® 244 FP, NF) | 14.0 |
| Talc (USP EP) | 7.4 |
| Eudragit ® L (methacrylic acid copolymer Type A, NF EP) | 17.9 |
| Triethyl citrate (NF) | 3.6 |
| Polyethylene oxide (Polyox ® WSR coagulant LEO, NF) | 33.3 |
| Povidone (K30, USP) | 3.4 |
| Total | 211.2 |

A comparator composition (Composition 4) which was essentially the same as Composition 3, but with no gelling agent-containing bead component, was prepared by blending IR beads as described in section 1.2; and CR beads as described in section 1.4 in a ratio of 20:80 (IR:CR) based on hydrocodone bitartrate content and filling the resultant blend into size 0 hard gelatin capsules to produce compositions having a strength of 20 mg/capsule.

Example 3

3.1 In Vitro Release Profiles

Figure 2:
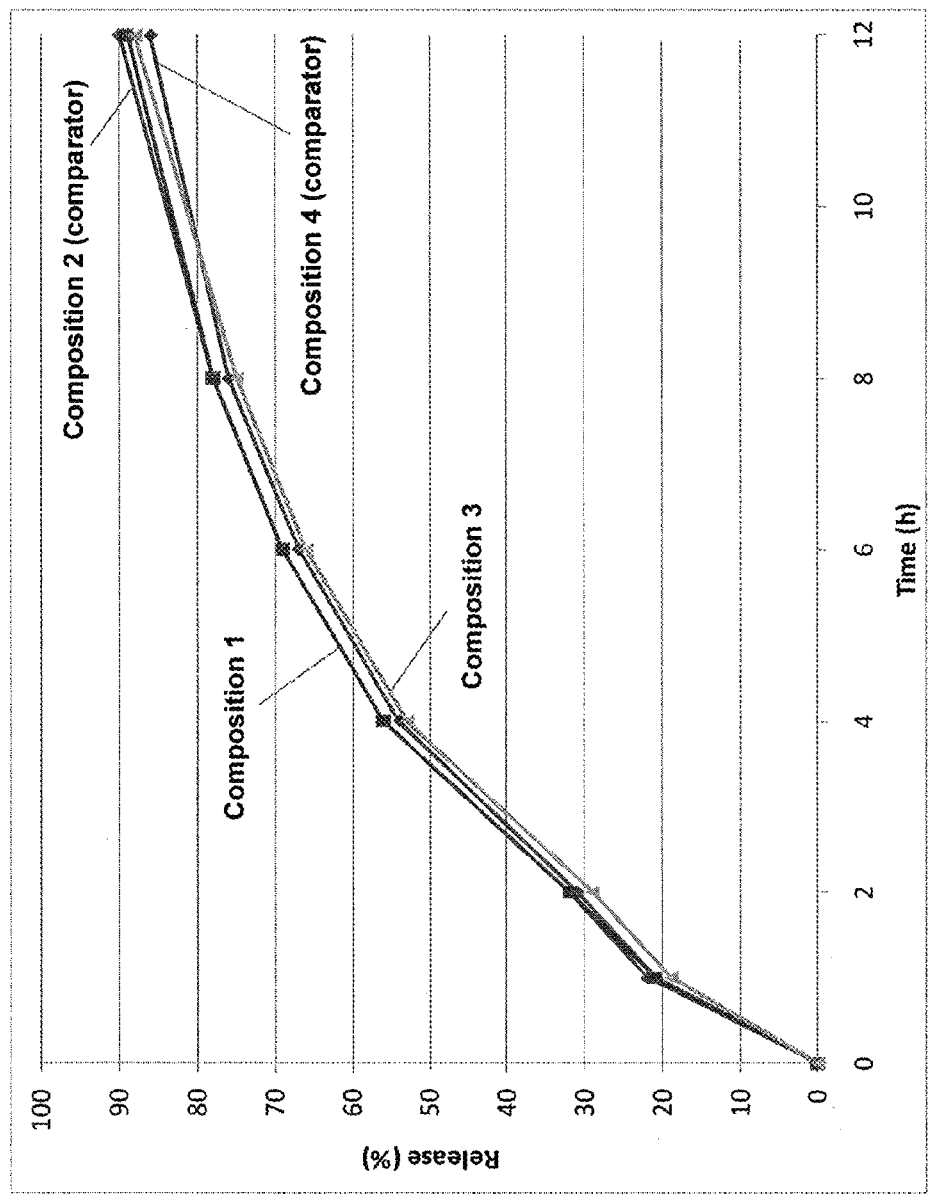
FIG. 2 is a graph illustrating the in vitro release of drug from two compositions of the invention compared to that of two comparator compositions which do not contain a gelling agent component.

FIG. 2 shows the in vitro release of hydrocodone bitartrate in phosphate buffer (pH 6.8) from Compositions 1 and 3 and from the respective comparators (Compositions 2 and 4). Active ingredient concentrations were determined by a validated HPLC method according to USP <711> using the following apparatus and conditions—USP Apparatus 1 (40-mesh basket); rotation: 100 rpm; timepoints: 1, 2, 4, 6, 8 and 12 hours; medium: 500 mL pH 6.8 phosphate buffer; temperature: 37.0+/−0.5° C. The control/comparator compositions contain the same amount of active ingredient and were designed to release the hydrocodone at substantially the same rate as the respective composition according to the invention. The primary difference between the comparators and the compositions of the invention was the absence of a population of beads containing a gelling agent in the former, the gelling agent (PEO) beads being a key feature of the latter (compositions of the invention). FIG. 2 shows that the in vitro release of drug from all four compositions is very similar. It is concluded from this data that the presence of the PEO beads in Compositions 1 and 3 did not impact the release of active ingredient.

3.2 In Vivo Release Profiles

Compositions 1 to 4 were administered orally as a single dose to healthy volunteers in a human pharmacokinetic study. Plasma concentrations of hydrocodone were determined at various time points post administration.

Figure 3:
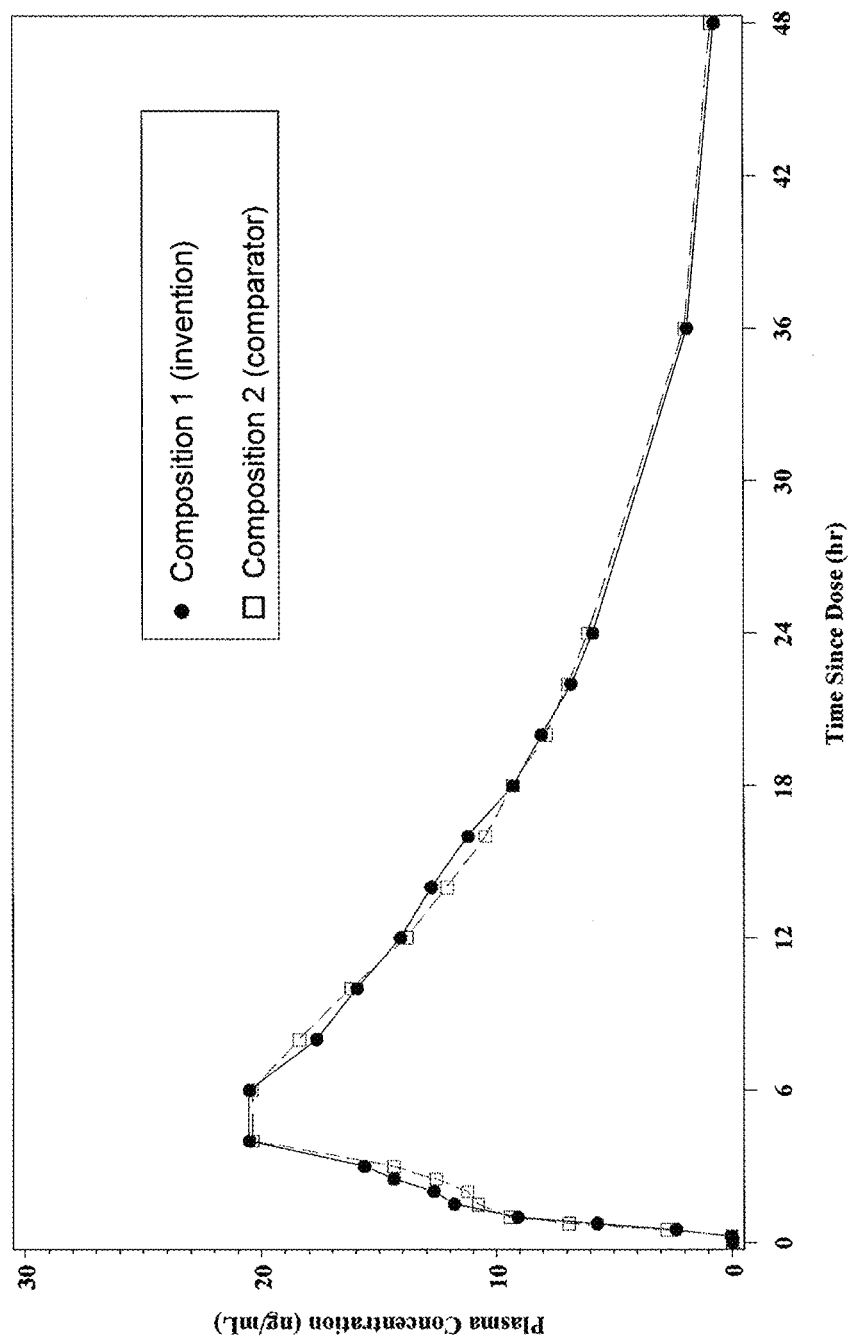
FIG. 3 is a graph illustrating the in vivo release of drug (mean plasma concentrations) from a composition according to the invention compared to that of a comparator composition which does not contain a gelling agent component.

FIG. 3 shows mean plasma concentration levels following administration of Composition 1 and Comparator Composition 2. FIG. 4 shows mean plasma concentration levels following administration of Composition 3 and Comparator Composition 4. Various PK parameters for the four compositions are summarised in Table 3.1 below.

TABLE 3.1

Summary of pharmacokinetic parameters.
(*Geometric mean ratio invention vs. control)

| Composition | $AUC_{(0-t)}$* | $C_{max}$* | $T_{max}$ (hrs) | $T_{1/2}$ (hrs) |
|---|---|---|---|---|
| 1 | 0.97 | 1.00 | 5 | 8.07 |
| 2 (Control) | — | — | 6 | 8.69 |
| 3 | 1.09 | 1.09 | 6 | 7.07 |
| 4 (Control) | — | — | 6 | 7.56 |

FIGS. 3 and 4 and Table 3.1 indicate that each pair of compositions (1 & 2; 3 & 4) are substantially bioequivalent. In other words, on the basis of this data the presence of the PEO beads (in Compositions 1 and 3) does not impact on the in vivo release of hydrocodone bitartrate from the composition.

Example 4

Abuse Mitigation—Attempt to Extract and Syringe API Using Small Volume of Water

Compositions of the invention, Compositions 5 and 6, were prepared as set out below.

4.1 PEO Abuse Deterrent Beads

Polyethylene oxide powder (av. m. wt. approx. 5,000,000) was applied to sugar sphere cores together with a PVP binder solution. The resultant PEO beads were coated with a coating comprising an ammonio methacrylate polymer (10% polymer weight gain). The binder solution, polymer suspension and overall content of the finished PEO beads are set out below in Tables 4.1 to 4.3 respectively. The methodology and processing parameters were substantially the same as those described in Example 1 above.

TABLE 4.1

Binder solution

| Material (Type/Grade) | Amount (mg/g) |
|---|---|
| PVP (Povidone K30, USP) | 84.5 |
| Water | 183.1 |
| Isopropyl alcohol (USP) | 732.4 |

TABLE 4.2

Coating suspension

| Material (Type/Grade) | Amount (mg/g) |
|---|---|
| Ammonio methacrylate copolymer, Type B (Eudragit RS; NF, EP) | 55.0 |
| Acetone (NF, EP) | 154.0 |
| Isopropyl alcohol (USP) | 724.4 |
| Water | 50.0 |
| Silicon dioxide (Syloid ® 244 FP) | 8.3 |
| Talc (USP) | 8.3 |

TABLE 4.3

Finished abuse deterrent beads

| Material (Type/Grade) | Amount (mg/g) |
|---|---|
| Sugar spheres (35/40 mesh, NF) | 347.9 |
| Polyethylene oxide (Polyox WSR coagulant LEO, NF) | 487.0 |
| PVP (Povidone K30, USP) | 50.0 |
| Ammonio methacrylate copolymer, Type B (Eudragit RS; NF, EP) | 88.5 |
| Silicon dioxide (Syloid ® 244 FP) | 13.4 |
| Talc (USP) | 13.4 |

4.2 Hydrocodone Bitartrate Capsules

Hydrocodone bitartrate compositions comprising 20% IR beads/80% CR beads (20:80 by active ingredient content) and an abuse deterrent component were prepared by blending PEO abuse deterrent beads (as per section 4.1), hydrocodone bitartrate immediate release (as per section 1.2) and hydrocodone bitartrate controlled release beads (as per sections 1.3) to provide the amounts shown in Table 4.4. Each blend was filled into hard gelatin capsules.

TABLE 4.4

Compositions 5 and 6 (*0EL or 0E el—ongated size 0)

| | Amount (mg/capsule) | |
|---|---|---|
| Material | Composition 5 | Composition 6 |
| Hydrocodone Bitartrate, USP | 20.0 | 50.0 |
| Sugar Spheres, NF | 135.0 | 234.4 |
| Hypromellose 2910, (6 cps) USP | 5.0 | 12.5 |
| Eudragit RS, NF, EP | 24.2 | 34.2 |
| Silicon Dioxide, NF (Syloid ® 244 FP) | 10.3 | 21.8 |
| Talc, USP | 3.6 | 5.2 |
| Polyethylene Oxide, NF (Polyox WSR Coagulant LEO) | 93.3 | 89.0 |
| Povidone K30, USP | 9.6 | 9.1 |
| Total | 301.0 | 456.2 |
| Capsule size | 0 | 0EL* |

4.4 Abuse Resistance

Figure 5B:
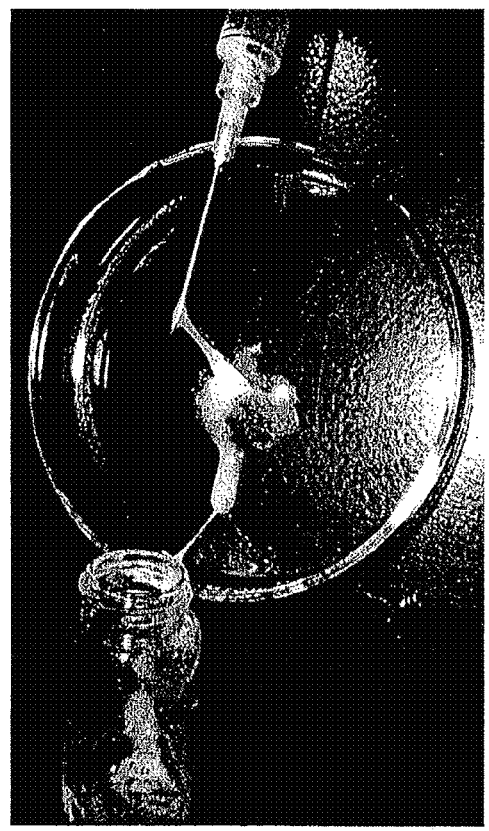
FIG. 5B depicts the gelling effect of a hydrocodone bitartrate composition of the invention upon mixing with 1 mL of water and the impact on ability to syringe the viscous mass produced.
Figure 5A:
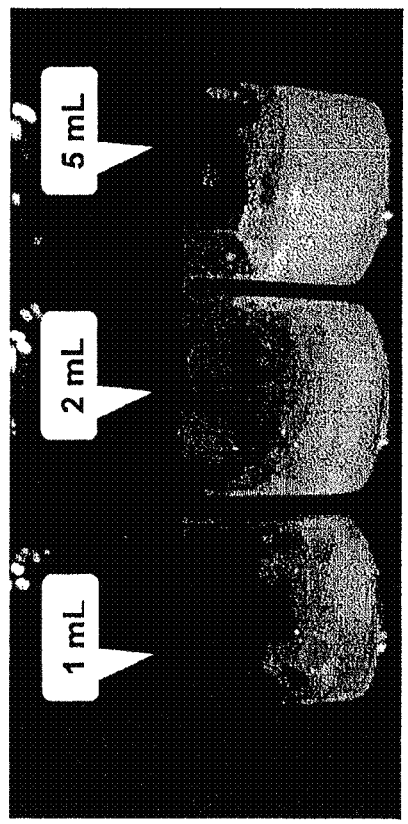
FIG. 5A depicts the gelling effect of a hydrocodone bitartrate composition of the invention upon mixing with various amounts of water (1, 2 & 5 mL).

The ability of a composition of the invention to deter attempts to produce an injectable form of the active ingredient was investigated by adding the contents of a capsule of Composition 5 (20 mg hydrocodone bitartrate) and Composition 6 (50 mg hydrocodone bitartrate) to several relatively small volumes of water (1, 2 and 5 mL respectively). The volumes used were chosen as representative of the syringe volumes that may typically be used by someone attempting to abuse a composition of this type. Samples were shaken for 10 minutes and observations were made at both ambient conditions and after samples had been placed in boiling water for 5 minutes. A clearly visible, viscous mass was produced in each case, see for example FIG. 5A (Composition 5; ambient conditions). With each of the three volumes investigated the gelling agent acted to absorb the entire volume of water, leaving no supernatant above the viscous material.

The material produced could not be filtered, thus providing no filtrate upon which to test injectability. An attempt was made to directly syringe the material produced when the composition is mixed with 1 mL of water (using an 18 gauge needle) was unsuccessful (see FIG. 5B). The viscosity of the material was such that nothing could be drawn up into the syringe.

Separating the active ingredient into small volumes of a suitable solvent could potentially facilitate an attempt to directly inject the extract. The results of this Example illustrate the abuse mitigating effects of a composition according to the invention.

Example 5

This Example investigates the behaviour of compositions of the invention, and a prior art comparator composition, when mixed with a relatively large volume of water. The intent being to simulate an attempt to extract the active ingredient from the respective dosage forms.

The methodology employed was as follows:
A single capsule of a hydrocodone bitartrate composition according to the invention (Compositions 5 and 6) or a single oxycodone tablet (see note [1] below), water (either 100 or 200 mL) and a magnetic stirring bar were placed in a glass flask with a screw on lid.
A pION, Spectra Rainbow Dynamic model, fibre optic probe (Pion, Inc—Billerica, Mass., USA) for determining the concentration of active ingredient was passed through the lid and placed in contact with the water. In the cases of both hydrocodone bitartrate and oxycodone the drug substance concentration was determined at 270-290 nm (20 mm path length, second derivative).
The stirring bar was activated and a timer was started.
The concentration of active ingredient was determined at various time points.
Photographs of the flask and contents were taken at t=0 and t=60 min.

([1] Oxycodone comparator consisted of Oxycontin® 30 mg and 80 mg tablets. According to the package insert for Oxycontin®, apart from oxycodone hydrochloride, each tablet contains the following inactive ingredients: ammonio methacrylate copolymer, hypromellose, lactose, magnesium stearate, polyethylene glycol 400, povidone, sodium hydroxide, sorbic acid, stearyl alcohol, talc, titanium dioxide and triacetin. The 30 mg tablets also contain: polysorbate 80, red iron oxide, yellow iron oxide and black iron oxide. The 80 mg tablets also contain: FD&C blue No. 2, hydroxypropyl cellulose and yellow iron oxide. (Oxycontin® is a registered trade mark of Purdue Pharma LP))

Figure 6B:
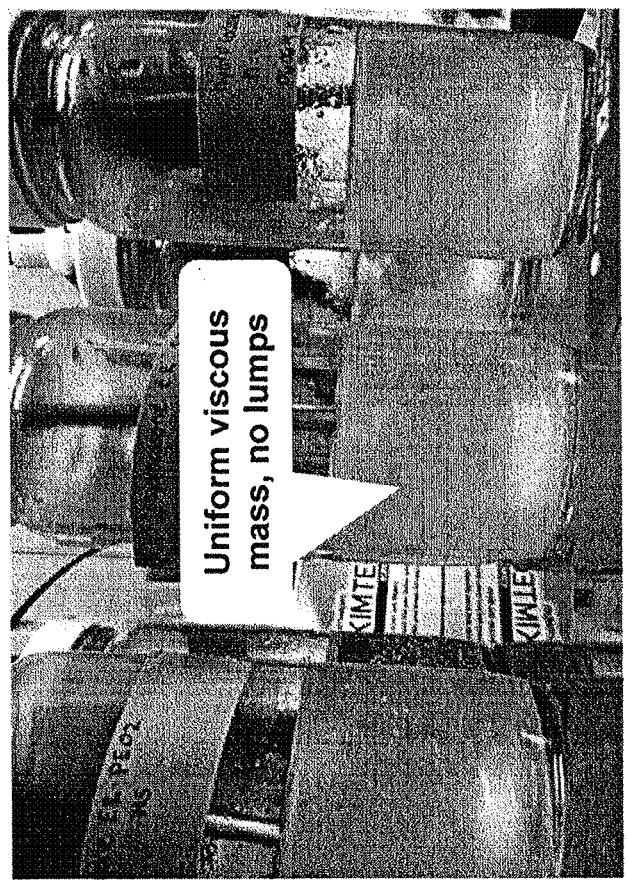
FIG. 6B depicts the composition shown in FIG. 6A after one hour.

FIGS. 6 and 7 illustrate the behaviour of hydrocodone bitartrate compositions according to the invention (Composition 5, 20 mg strength and Composition 6, 50 mg strength; in FIGS. 6 and 7 respectively) when mixed with water (100 mL or 200 mL) and stirred for 60 minutes.

Figure 6A:
FIG. 6A depicts the initial behaviour of a hydrocodone bitartrate composition of the invention (20 mg strength) in water (100 mL).
Figure 7B:
FIG. 7B depicts the compositions shown in FIG. 7A after one hour.

The contents of a capsule of Composition 5 were emptied out and added (unaltered) to 100 mL of water with stirring. With reference to FIG. 6A, it was observed that the water quickly started to turn turbid. The thickening of the liquid phase was clearly visible. After one hour (FIG. 6B) the entire volume of water had become cloudy and almost opaque. No supernatant was formed and the visual appearance of the entire volume was uniform. The experiment was repeated with n=3 capsules, with similar results observed each time.

Figure 7A:
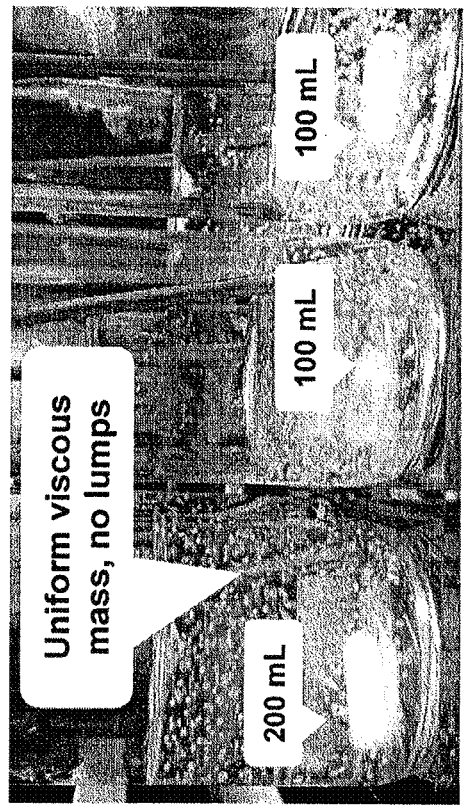
FIG. 7A depicts the initial behaviour of hydrocodone bitartrate compositions of the invention (50 mg strength) in water (100 or 200 mL).

Similar behaviour was observed when Composition 6 of the invention was added to 100 or 200 mL of water, see FIGS. 7A (t=0) and 7B (t=60 min). Again the experiment was repeated with n=3 capsules, with similar results observed each time.

Figure 8B:
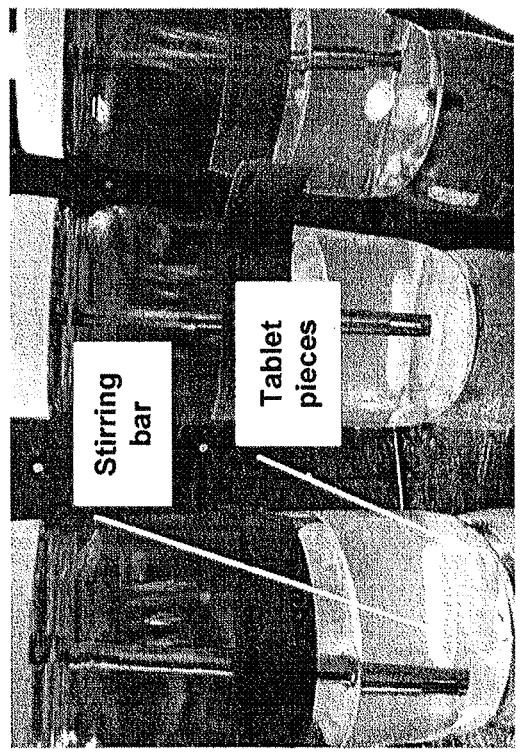
FIG. 8B depicts a comparative example showing the behaviour of a prior art oxycodone tablet (80 mg) comprising a gelling agent in water (100 mL).
Figure 8A:
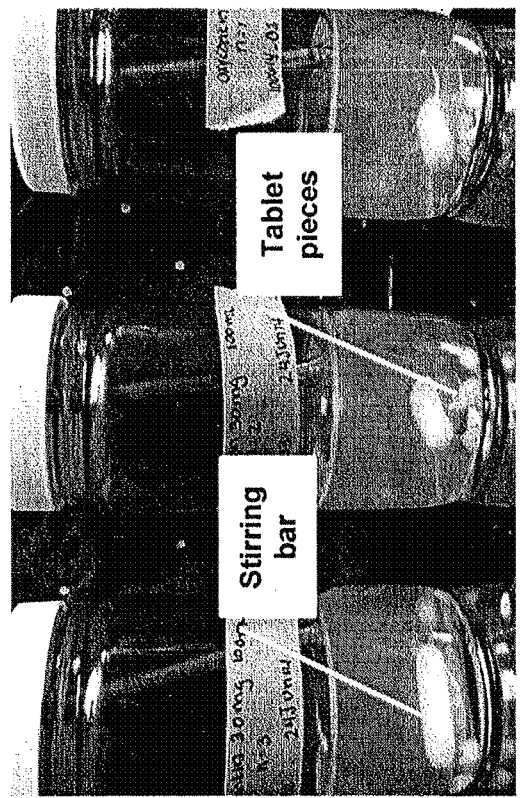
FIG. 8A depicts a comparative example showing the behaviour of a prior art oxycodone tablet (30 mg) comprising a gelling agent in water (100 mL).

FIG. 8 (comparative example) shows what happens when an oxycodone tablet (Composition 7: Oxycontin, 30 mg—FIG. 8A; Composition 8: Oxycontin 80 mg—FIG. 8B) comprising a gelling agent is added to water (100 mL) and stirred for 30 minutes.

In order to mimic the actions of a potential abuser, the Oxycontin® tablets were cut into six approximately equal sized pieces to expose the interior portions of the dosage form. Upon addition of the tablet pieces to the water some gelling on the exposed surfaces was observed and some clouding of the water developed. At the one hour time point the tablet pieces were still clearly visible on the bottom of the flask. The liquid above the tablet pieces was readily drawn off for analysis and no change in viscosity was apparent. The experiment was repeated with n=3 Oxycontin® tablets, with similar results observed each time.

Qualitatively similar behaviour, as that seen with Oxycontin® tablets, was observed for polyethylene oxide based hydrocodone bitartrate mini-tablets and extruded pellets.

The use of a fibre optic probe enabled the release of active ingredient to be followed without having to extract a sample from the test material over the time period during which the photographs (FIG. 6A, 6B, 7A, 7B) were taken. The relative behaviour of the compositions of the invention depicted in FIGS. 6 and 7 and the prior art composition depicted in FIG. 8 are illustrated by the data set out in Table 5.1 below and shown in FIG. 9.

TABLE 5.1

Amount of drug extracted from compositions of the invention and two comparator compositions. (*Comparator compositions)

| Composition | Amount of drug in solution (mg) | Percentage of label claim (% (w/w)) |
| --- | --- | --- |
| 5 | 4.6 | 23.0 |
| 6 | 11.8 | 23.6 |
| 7* | 19.9 | 66.2 |
| 8* | 41.7 | 52.1 |

Figure 9:
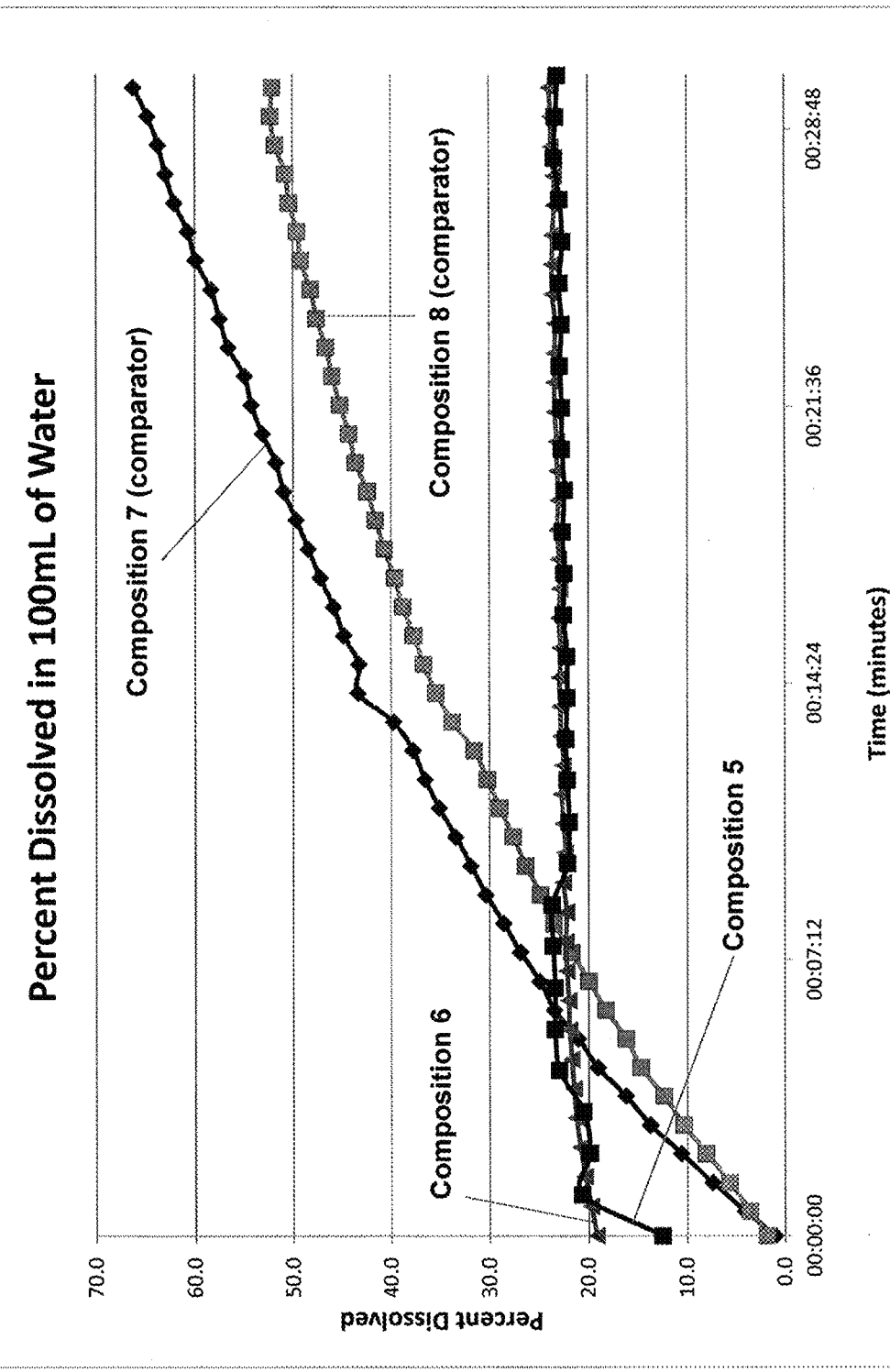
FIG. 9 is a graph illustrating the extraction of drug substance from hydrocodone bitartrate compositions of the invention compared to prior art oxycodone compositions.

The data in Table 5.1 and FIG. 9 indicates that considerably more active ingredient was released from the comparator compositions (7 and 8). The release from the compositions of the invention corresponds to the 20% IR active ingredient component of each composition. However, it should be noted that whilst this fraction of hydrocodone was released from the composition, the highly viscous and uniform nature of the gel produced in the entire volume of water used means that it would be extremely difficult, if not impossible, for the release active ingredient to be separated from the gel.

GENERAL CONCLUSIONS FROM THE EXAMPLES

The gelling-agent component of the compositions of the invention does not adversely impact the in vitro or in vivo release of pharmaceutically active ingredient from the composition (intact and not subjected to any tampering). In particular, the presence of the gelling agent-containing beads does not have any adverse effect on the bioavailability of the active ingredient.

Compositions of the invention exhibit a gelling behaviour when added to water, even in the absence of any tampering i.e. the composition behaves the same whether the gelling agent-containing beads are added to water intact or are crushed first. When mixed with a relatively small volume of water a viscous mass is formed which cannot be drawn up into a syringe. This thwarts attempts to inject the entire contents of the composition.

On the other hand, attempting to extract the active ingredient by mixing the composition with a relatively large volume of water (in order to dissolve the drug and separate it from the remaining constituents by decanting and/or filtering) produces a uniform, dispersed, viscous mass, entrapping any dissolved drug and any intact beads.

The invention claimed is:

1. A method for the treatment of pain comprising administering to a subject in need thereof a composition comprising a first population and a second population of beads;
the first population of beads being substantially free of polyethylene oxide and comprising an active selected from the group consisting of benzylmorphine, bezitramide, buprenorphine, butorphanol, carfentanil, clonitazene, codeine, desomorphine, dextromoramide, dezocine, diacetylmorphine, diampromide, diamorphone, dihydrocodeine, dihydromorphine, dimenoxadol, dimepheptanol, dimethylthiambutene, diphenoxylate, dioxaphetyl butyrate, diprenorphine, dipipanone, eptazocine, ethoheptazine, ethylmethylthiambutene, ethylmorphine, etonitazene, etorphine, dihydroetorphine, fentanyl, hydrocodone, hydromorphone, β-hydroxy-3-methylfentanyl, hydroxypethidine, isomethadone, ketobemidone, levo-α-acetylmethadol, levorphanol, levophenacylmorphan, lofentanil, meperidine, meptazinol, metazocine, methadone, metopon, morphine, myrophine, nalmefene, narceine, nicomorphine, norlevorphanol, normethadone, nalorphine, nalbuphene, normorphine, norpipanone, o-methylnaltrexone, opium, oxycodone, oxymorphone, papaveretum, pentazocine, pethidine, phenadoxone, phenomorphan, phenazocine, phenoperidine, piminodine, piritramide, proheptazine, promedol, properidine, propoxyphene, remifentanil, sufentanil, tilidine, and tramadol, or pharmaceutically acceptable salts thereof, and
the second population of beads being substantially free of any pharmaceutically active ingredient and comprising polyethylene oxide and a permeable or semi-permeable coating selected from the group consisting of an ammonio methacrylate copolymer, a methacrylic acid copolymer and a mixture thereof.

2. The method of claim 1, wherein said second population of beads further comprises povidone.

3. The method of claim 1, wherein the polyethylene oxide is present in particulate form.

4. The method of claim 1, wherein the active is selected from the group consisting of codeine, dihydrocodeine, hydrocodone, methadone, morphine and oxycodone or pharmaceutically acceptable salts thereof.

5. The method of claim 4, wherein the active is hydrocodone bitartrate.

6. The method of claim 1, wherein the active is present in an amount of from 5 to 250 mg.

\* \* \* \* \*